(12) United States Patent
Trapero Martin et al.

(10) Patent No.: US 11,166,635 B2
(45) Date of Patent: Nov. 9, 2021

(54) ECG AND BIOIMPEDANCE BASED GLUCOSE MONITORING SYSTEM

(71) Applicant: ANEXA LABS LLC, Mountain View, CA (US)

(72) Inventors: Ana Trapero Martin, Salamanca (ES); Michael Daniel Vermeer, Kitchener (CA); Mathew Asselin, Toronto (CA); Joel Steven Ironstone, Toronto (CA); Alexey Reykhert, Omsk (RU)

(73) Assignee: ANEXA LABS LLC, Mountain View, CA (US)

( * ) Notice: Subject to any disclaimer, the term of this patent is extended or adjusted under 35 U.S.C. 154(b) by 0 days.

(21) Appl. No.: 17/160,990

(22) Filed: Jan. 28, 2021

(65) Prior Publication Data
US 2021/0228090 A1 Jul. 29, 2021

Related U.S. Application Data

(60) Provisional application No. 62/967,429, filed on Jan. 29, 2020.

(51) Int. Cl.
*A61B 5/0205* (2006.01)
*A61B 5/00* (2006.01)
*G16H 40/67* (2018.01)
*G16H 10/60* (2018.01)
(Continued)

(52) U.S. Cl.
CPC .......... *A61B 5/0205* (2013.01); *A61B 5/4875* (2013.01); *A61B 5/6833* (2013.01);
(Continued)

(58) Field of Classification Search
CPC .............. A61B 5/0205; A61B 5/48755; A61B 5/282; A61B 5/339; A61B 5/6833; A61B 5/355;
(Continued)

(56) References Cited

U.S. PATENT DOCUMENTS

2003/0032989 A1 2/2003 Herleikson
2005/0202797 A1 9/2005 Sorrells
(Continued)

OTHER PUBLICATIONS

S. Shin, S. Lee, T. Lee, K. Lee, Y. S. Lee and H. Kang, "Two electrode based healthcare device for continuously monitoring ECG and BIA signals," 2018 IEEE EMBS International Conference on Biomedical & Health Informatics (BHI), 2018, pp. 141-144, doi: 10.1109/BHI.2018.8333389 (Year: 2018).*
(Continued)

*Primary Examiner* — Lynsey C Eiseman
*Assistant Examiner* — Amanda L Steinberg
(74) *Attorney, Agent, or Firm* — Nixon Peabody LLP

(57) ABSTRACT

A glucose monitoring system can make use of electrocardiograph (ECG) data and bioimpedance data acquired from a wearable device. The ECG data and bioimpedance data can each be processed to obtain a glucose level. These values can be processed together to obtain an adapted glucose value. In some cases, photoplethysmography data can also be used to assist in processing of the ECG data. The various types of data can be acquired from sensors on a wearable device. The wearable device can be removably coupled to a user's skin, such as via an adhesive substrate. In some cases, the wearable device can include a reusable electronics module that couples to replaceable electrodes on a replaceable adhesive substrate.

18 Claims, 19 Drawing Sheets

(51) Int. Cl.

| | |
|---|---|
| *G16H 50/30* | (2018.01) |
| *G16H 50/70* | (2018.01) |
| *A61B 5/0537* | (2021.01) |
| *A61B 5/145* | (2006.01) |
| *A61B 5/282* | (2021.01) |
| *A61B 5/339* | (2021.01) |
| *A61B 5/358* | (2021.01) |
| *A61B 5/352* | (2021.01) |
| *A61B 5/355* | (2021.01) |
| *A61B 5/1495* | (2006.01) |
| *A61B 5/333* | (2021.01) |

(52) U.S. Cl.
CPC ............ *G16H 10/60* (2018.01); *G16H 40/67* (2018.01); *G16H 50/30* (2018.01); *G16H 50/70* (2018.01); *A61B 5/0537* (2013.01); *A61B 5/1495* (2013.01); *A61B 5/14503* (2013.01); *A61B 5/14532* (2013.01); *A61B 5/282* (2021.01); *A61B 5/333* (2021.01); *A61B 5/339* (2021.01); *A61B 5/352* (2021.01); *A61B 5/355* (2021.01); *A61B 5/358* (2021.01); *A61B 2560/0252* (2013.01); *A61B 2562/0209* (2013.01); *A61B 2562/063* (2013.01)

(58) Field of Classification Search
CPC ......... A61B 5/358; A61B 5/352; A61B 5/333; A61B 5/0537; A61B 5/14503; A61B 5/14532; A61B 5/1495
See application file for complete search history.

(56) References Cited

U.S. PATENT DOCUMENTS

| | | |
|---|---|---|
| 2011/0301441 A1 | 12/2011 | Bandic |
| 2013/0096549 A1 | 4/2013 | Organ |
| 2013/0102920 A1 | 4/2013 | Fan |
| 2013/0218252 A1 | 8/2013 | Kaib |
| 2014/0257122 A1* | 9/2014 | Ong .................. A61B 5/02405 600/515 |
| 2014/0288385 A1 | 9/2014 | Amurther |
| 2016/0120433 A1* | 5/2016 | Hughes .................. G16H 80/00 600/483 |
| 2016/0317067 A1 | 11/2016 | Lee |
| 2017/0188872 A1 | 7/2017 | Hughes |
| 2017/0325724 A1 | 11/2017 | Wang |
| 2018/0333306 A1 | 11/2018 | Ng |
| 2020/0100693 A1 | 4/2020 | Velo |

OTHER PUBLICATIONS

Porumb, M., Stranges, S., Pescapè, A. et al. Precision Medicine and Artificial Intelligence: A Pilot Study on Deep Learning for Hypoglycemic Events Detection based on ECG. Sci Rep 10, 170 (2020). https://doi.org/10.1038/s41598-019-56927-5 (Year: 2020).*

D. Huber et al., "Multi-sensor data fusion for non-invasive continuous glucose monitoring," 2007 10th International Conference on Information Fusion, 2007, pp. 1-10, doi: 10.1109/ICIF.2007.4408095 (Year: 2007).*

Tobore I, Li J, Kandwal A, Yuhang L, Nie Z, Wang L. Statistical and spectral analysis of ECG signal towards achieving non-invasive blood glucose monitoring. BMC Med Inform Decis Mak. Dec. 19, 2019;19(Suppl 6):266. doi: 10.1186/s12911-019-0959-9. PMID: 31856801; PMCID: PMC6921435 (Year: 2019).*

Cordeiro, R., 2019. Non-Invasive Hyperglycemia Detection Using ECG and Deep Learning. Master of Science. San Jose State University. (Year: 2019).*

International Search Report and Written Opinion in International Application No. PCT/US2021/015408, dated Apr. 23, 2021 (16 pages).

* cited by examiner

ECG AND BIOIMPEDANCE BASED GLUCOSE MONITORING SYSTEM

CROSS REFERENCE TO RELATED APPLICATIONS

The present application claims the benefit of U.S. Provisional Patent Application No. 62/967,429 filed Jan. 29, 2020 and entitled "MULTI-USE ELECTRODES IN A WEARABLE HEALTH MONITORING DEVICE," which is hereby incorporated by reference in its entirety.

TECHNICAL FIELD

The present disclosure relates to medical devices generally and more specifically to wearable medical devices.

BACKGROUND

The following description includes information that may be useful in understanding the present invention. It is not an admission that any of the information provided herein is prior art or relevant to the presently claimed invention, or that any publication specifically or implicitly referenced is prior art.

Body composition is an important indicator of health. Having too high of body fat percentage can lead to various problems, such as arthritis of the knees, type 2 diabetes, gynecological problems, gallstones, asthma, heart disease, and even depression. Monitoring of body fat percentage, among other physiological metrics, can be useful to the prevention of and early detection of various medical problems. Additionally, measurement of electrical activity within the body, such as electrical activity of the heart and bioimpedance (BI), can be useful physiological metrics to monitor.

Recent advances in electronics miniaturization, faster microprocessors, new sensor technologies, ubiquitous wireless networks, and artificial intelligence (AI)-based data analysis techniques have enabled the development of wearable devices for remote patient monitoring. Achieving reliable and high integrity recording however remains a challenge, especially under daily-life activities. Wearable systems have been introduced in an attempt to reduce size, improve comfort and extend the duration for monitoring. Wearable patches can monitor health metrics using a plurality of on-board sensors and detect life threatening health changes using AI algorithms that work in real-time.

Current technologies for monitoring electrocardiogram (ECG) data and for monitoring BI data do so using a large number of electrodes. Current technology makes use of at least a pair of electrodes, although often more, for ECG measurements, and at least two pairs of electrodes for BI measurements. While some technology may use only a single pair of electrodes for BI measurements, doing so results in low-precision BI measurements that may be unsuitable for most applications. Thus, measurement of ECG data and BI data currently makes use of at least six different electrodes.

To ensure accurate and useful measurements, there are minimum sizes for the electrodes contact area and minimum distances between adjacent electrodes. Thus, current technology limits for a device that would measure both ECG data and BI data would be limited to being no smaller than a minimum size capable of housing all six electrodes, with necessary spacing, and other required electronics. Additionally, since the accuracy of the measurements is dependent on the electrical conduction between the user and the electrodes, each additional electrode in a system adds another potential point of failure (e.g., due to an incomplete or otherwise non-optimally functioning electrical connection).

There is a need for an improved wearable device capable of collecting both ECG and BI measurements, such as a device capable of collecting these measurements with fewer than six electrodes and in a smaller form factor.

SUMMARY

Certain aspects and features of the present disclosure relate to a system for acquiring electrocardiograph (ECG) data and bioimpedance (BI) data using at least one pair of shared electrodes. The system, referred to herein as ECG/BI measurement system, can simultaneously or near-simultaneously acquire ECG measurements and perform BI spectroscopy or other BI monitoring. The use of at least one pair of shared electrodes permits ECG and BI data acquisition with only a single pair of electrodes or two pairs of electrodes. When two pairs of electrodes are used, one or both pairs can be shared between ECG data acquisition and BI data acquisition.

According to certain aspects of the present disclosure, BI monitoring can be performed on the body generally, and/or for any particular location on the body, such as on the chest (e.g., when the ECG/BI measurement system is incorporated into a smart patch worn on the user's chest). Although two electrodes can be used to inject and measure current, a tetrapolar (4-electrode) configuration can reduce measurement error that may be induced by electrode-tissue impedance (ETI), which can be an issue in bipolar electrode configuration systems. An impedance recording can be obtained using a specific electrode configuration where the electrodes are placed on the surface of the upper torso. Impedance can be measured by passing a small alternating current (AC) between any pair of electrodes connected to the skin. Thus, the measured impedance resulting from the voltage measured between another pair of electrodes reflects the ability of biological tissue to impede electric current.

By injecting a low-frequency AC current to the chest area, a voltage proportional to the tissue impedance in that area can be measured. Generally, bioimpedance recordings are used to estimate various physio-chemical and physiological states of the user, such as cardiac rhythm, respiration, tissue hydration and body composition. Therefore, certain aspects of the present disclosure can be useful for the tracking of various physiological metrics, such as cardiopulmonary metrics.

Bioimpedance measurements are composed of tissue resistance and tissue reactance, which alone or combined can be used to determine different health metrics. Resistance is based on the dissipation of energy by the tissue, and reactance is based on the storage of energy by the tissue. Thus, each of these characteristics can change depending on the characteristics of the underlying tissue. In some cases, a change in one or both of these bioelectrical characteristics can be correlated with a change in other physiological characteristics of the underlying tissue. In some cases, a change in one of these bioelectrical characteristics (e.g., resistance) can be sufficient to determine a desired characteristic of the underlying tissue, without necessarily determining a change in the other bioelectrical characteristics (e.g., reactance). Certain aspects of the present disclosure utilize resistance measures with low frequency readouts (e.g., at or below approximately 10 kHz, or within 1, 2, or 3 kHz of 10 kHz). In some cases, both resistance and reactance recordings can be extracted from the microprocessor calculations.

Using at least one pair of electrodes, an ECG sensor can measure the surface potential difference between the electrodes. In some cases, the pair of electrodes can be placed in a suitable location (e.g., on a chest of a user, such as above a heart of the user) to measure electrical signals of the heart. The ECG measurements can be made over a short-term duration (e.g., on the order of seconds, minutes, or hours) or a long-term duration (e.g., on the order of days, tens of days, or more). With appropriate placement of the device on the chest, a very clear distinction of electrocardiographic waves can be achieved, allowing for high quality ECG recording that is sufficient for medical analysis. Some patch positions can be better for monitoring atrial activities, like the morphology of the P wave. ECG sensors can measure the action potentials generated during the cardiac activity of a user, and can be used to calculate various physiological metrics, such as heart rate. Consequently, the cardiac wave and QRS complex are usually calculated by first detecting the R wave. Therefore, processing the bipolar differential measurement of the ECG includes amplification and feature/parameter extraction, as well as filtering biopotential signals. The ECG/BI measurement system can implement filters to promote a high signal-to-noise ratio, which permits even small R-peaks to be discerned in noisy conditions like those formed through motion or imprecise placement of electrodes. In some cases, because high-frequency noise can be a primary cause of ECG signal distortion, the ECG/BI measurement system can include a low-pass filter to reduce the overall processing system complexity. Additionally, notch filters can be included to remove unwanted environmental noise, such as line frequency of power in homes, healthcare institutions, and the like.

Raw data from signals sensed via the one or more pairs of electrodes can be processed into processed waves. These processed waves can be compressed to enable efficient transmission and data storage without losing important diagnostic information. In some cases, such compression can be based on feature/parameter extraction methods which, to a certain extent, can accurately represent the heart's electrical activity.

While a single pair of electrodes can be used to generate single-lead ECG measurements, in some cases two or more pairs of electrodes can be used for the purpose of multiple lead ECG measurements. When measuring ECG with two or more different pairs of electrodes, each pair is attached to different channels of the ECG sensor on the printed circuit board (PCB). In some cases, two sets of electrode pairs can be implemented in a nested linear array, in which case a pair of inner electrodes is located between and collinear with the electrodes of a pair of outer electrodes. In such cases, two ECG measurements can be obtained either using the inner and outer pairs of electrodes, or using first and second alternate pairs of electrodes. In some cases, each of these electrode groupings can result in different ECG signals. In some cases, sequential ECG measurements can be taken using different electrode groupings (e.g., first and second ECG signals taken using inner and outer pairs of electrodes, then third and fourth ECG signals taken using first and second alternate pairs of electrodes). The multiple readings from two or more ECG channels can be processed and correlated to reduce noise in the measurements, as well as to increase details in the extracted curves. Moreover, in addition to a single-lead measurement, one of the remaining electrodes might be used as a ground reference input to the ECG signal.

The sharing of electrodes permits wearable devices employing such an ECG/BI measurement system to be made into smaller, more comfortable, and more inconspicuous formats, as well as decreasing the number of points of failure in electrical conductivity between the system and the user. Thus, such wearable devices can be constructed more easily (e.g., with fewer parts, fewer connections, and/or fewer metal components). Additionally, the increased convenience to a user may improve user compliance, which can lead to more data acquisition, improved data acquisition over time (e.g., via further AI training), and improved ability for the wearable device to detect a medical condition or otherwise provide actionable feedback or data.

In a simultaneous measurement scheme, ECG and BI data are measured simultaneously. In this simultaneous measurement scheme, ECG data and BI data are separately extracted from a signal sensed across a single shared pair of electrodes, while another pair of electrodes is being driven with a supply current (e.g., an injection current). In a sequential measurement scheme, ECG and BI data can be measured sequentially. In this sequential measurement scheme, internal switching can automatically switch a shared pair of electrodes between ECG-measuring circuitry and BI-measuring circuitry, such as based on a clock signal or other trigger.

The acquisition of ECG data and BI data form a single, wearable device also facilitates the accurate measurement of blood glucose levels without the need for invasive techniques, such as finger pricks and the like. Blood glucose level can be estimated from ECG alone, from BI data alone, or from both ECG data and BI data. In some cases, a blood glucose level estimate using ECG data and a blood glucose estimate using BI data can be both used to generate a single blood glucose estimation, which may be a high-accuracy blood glucose estimation.

Furthermore, certain aspects of the present disclosure may also be useful for determining heart rate, other features of an electrocardiogram, fluid volumes, and body cell mass. These metrics may be helpful for monitoring HIV-infected individuals, post-surgical patients, or other individuals that may benefit from such monitoring.

The acquisition of ECG data and BI data from a single, wearable device can also facilitate analysis, estimation, and prediction about other physiological metrics or medical conditions of an individual.

Certain aspects and features of the present disclosure permit a wearable device employing an ECG/BI measurement system to be manufactured in small form factors capable of being worn comfortably and inconspicuously for extended periods of time, while simultaneously collecting useful ECG and BI data.

BRIEF DESCRIPTION OF THE DRAWINGS

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

DETAILED DESCRIPTION

Figure 1:
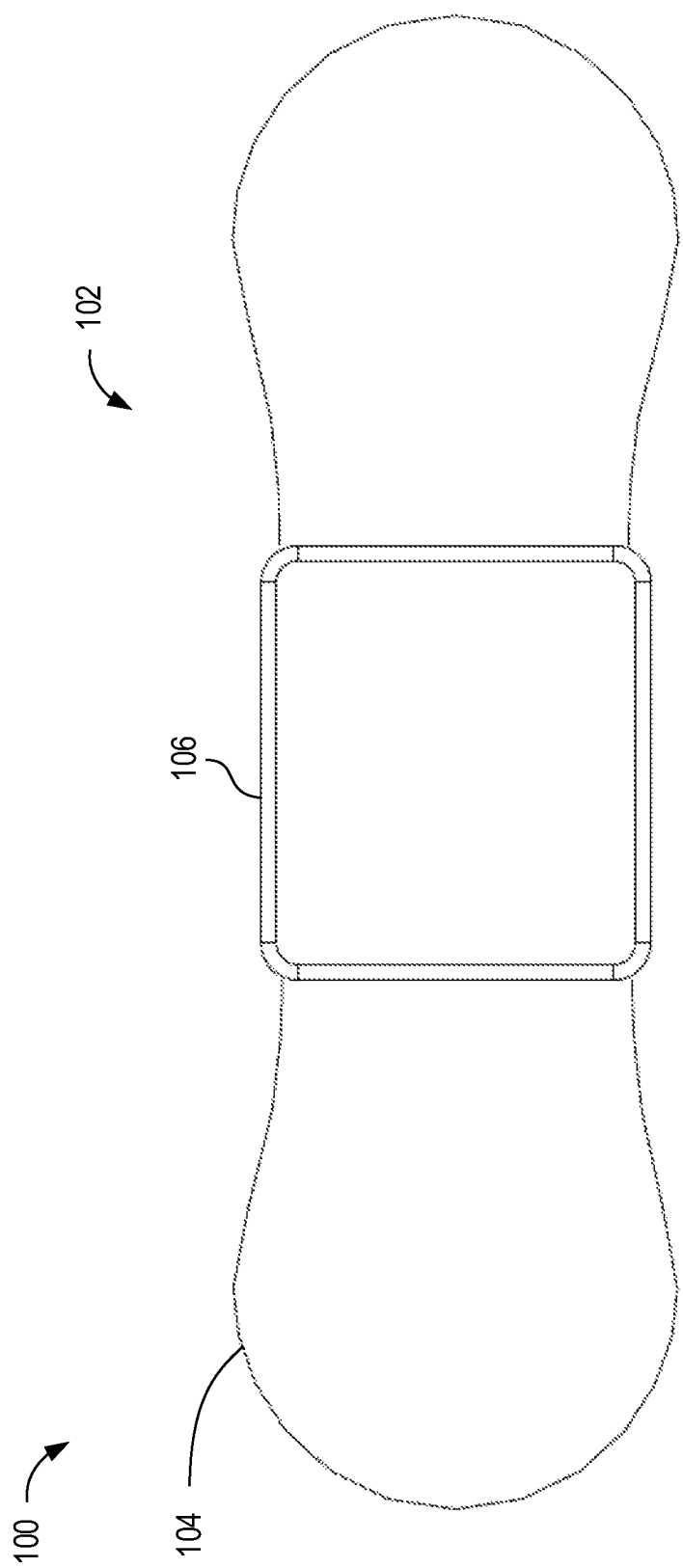
FIG. 1 is a top view of a smart patch employing an ECG/BI measurement system, according to certain aspects of the present disclosure.

Certain aspects and features of the present disclosure relate to a system for acquiring electrocardiograph (ECG) data and bioimpedance (BI) data. The system (an ECG/BI measurement system) can make use of as few as one or two pairs of electrodes through the sharing of electrodes for both ECG and BI data acquisition. This sharing of electrodes permits wearable devices employing the ECG/BI measurement system to be made into smaller, more comfortable, and more inconspicuous formats, as well as decreasing the number of points of failure in electrical conductivity between the system and the user. In some cases, ECG data and BI data are separately extracted from a measured signal across a single shared pair of electrodes, while another pair of electrodes is being driven with a supply current. In other cases, internal switching can automatically switch a shared pair of electrodes between ECG-measuring circuitry and BI-measuring circuitry, such as based on a clock signal or other trigger. An ECG/BI measurement system can be incorporated into any suitable device, such as a wearable device, such as a smart patch or smartwatch. Other devices can employ the disclosed ECG/BI measurement system.

Wearable systems have limited space available for contact with a patient. For instance, a wearable patch is most effective when it is as small and unobtrusive as possible to the patient, because the patient will be more likely to wear the patch long term and there is a lower likelihood of the wearable device being inadvertently dislodged or otherwise inadvertently disabled. Accordingly, reducing the required surface area of contact with the patient is important to its effective and continuous use. Furthermore, minimizing the weight of a wearable device is important so the method of securing the wearable device to the user can be less harmful to the skin of the user. For example, a light-weight wearable patch can ensure an adhesive layer of the patch is able to retain the patch on the skin. Thus, the lighter the patch, the less harmful or "sticky" the adhesive must be to retain the patch on the skin.

Therefore, minimizing the electrical, and especially conductive, components, as well as minimizing the required surface area of contact with the patient in a wearable device can be important. However, the more functions and health indications that are monitored by the wearable health monitoring devices, the more effective and useful they are. But each new function usually requires additional hardware, and thus increases the weight of the wearable device. Therefore, for wearable devices, there is a natural tension between minimizing size and weight, while maximizing health monitoring features.

Similarly, certain forms of wearable devices naturally benefit from small size and contact area with a user. For example, wearable devices like watches only make contact with a user through the back of the watch body in contact with the wrist and the watch band, which are relatively small areas. Additionally, most other wearable devices are most effective and useful when their size and weight are minimized. However, most additional features require additional hardware.

For instance, wearable devices that monitor ECG features require electrodes that make contact with the user's skin. Similarly, performing bioimpedance spectroscopy or bioimpedance analysis on a patient requires additional electrodes and circuitry to monitor a variety of health metrics associated with the BI of the individual. Accordingly, the many electrodes from both functions makes it difficult to design a small wearable device that can monitor both functions, and can monitor health signs that require both ECG data and BI data.

According to certain aspects of the present disclosure, integration of ECG measurement and BI measurement is achieved in the same hardware using shared electrodes. Thus, the system can detect ECG electrical activity, while also performing BI analysis. BI analysis can include traditional single-frequency analysis (e.g., measurement of impedance at a specified frequency, such as 50 kHz), or multi-frequency bioimpedance spectroscopy (e.g., injection of current at multiple frequencies and the measurement of impedance at each frequency).

The sharing of electrodes for both ECG monitoring and BI analysis can be achieved through either filter-based extraction techniques or automated switching of the shared electrodes between the ECG circuitry and BI circuitry.

In some examples, both ECG monitoring and BI analysis can be performed using only two electrodes or only four electrodes. This reduction in the number of electrodes needed is quite advantageous, at least because electrodes are made of conductive materials that require a minimum surface area and level of contact with a patient's skin to be effective. Accordingly, each additional electrode or electrode pair added to the wearable device (e.g. the patch) requires quite significant additional surface area—to the point at which three electrode pairs that are effective for monitoring may make a wearable device too large to be comfortably and continuously worn by a user. Accordingly, the disclosed systems and methods have been developed to monitor ECG and BI using only two electrodes (e.g., one electrode pair, or a bipolar configuration) or four electrodes (e.g., two electrode pairs, or a tetrapolar configuration).

The ability to perform both ECG readings and bioimpedance spectroscopy using a wearable device with two or four electrodes can be particularly advantageous for monitoring blood glucose levels. It has been discovered that a near-clinically accurate glucose reading can be obtained by combining the results from an ECG-based method for detecting blood glucose levels and a bioimpedance spectroscopy-based method for detecting blood glucose levels as disclosed herein. Accordingly, certain aspects and features of the present disclosure permit the measurement of blood glucose levels using only one or two pairs of electrodes, thus permitting such a system to be embodied in a relatively small wearable device that can be continuously worn to accurately measure blood glucose levels over time.

As used herein, the term "glucose level" is inclusive of a glucose value (e.g., a specific value representative of an amount of blood sugar within a volume of blood), a range (e.g., greater than a threshold value, less than a threshold value, or between two threshold values), or a categorical variable or enumerated range (e.g., "high," "normal," and "low").

Disclosed herein are systems and methods for the non-invasive monitoring of blood glucose levels with a level of accuracy that can replace invasive methods, such as finger prick devices and others. In some examples, glucose levels are determined using a patient's electrocardiogram (ECG) data. Additionally, glucose levels may additionally be determined using a bioimpedance spectroscopy-based method and then combined with glucose levels determined using the ECG data to output a more accurate blood glucose level.

Accordingly, it has been discovered that blood glucose levels may be determined entirely from the ECG waveform. For instance, certain ECG features (e.g. QRS complex, ST segment, QT time interval, etc.) were unexpectedly discovered to be closely correlated with the blood glucose level value, and thus could be used to determine a blood glucose level value. This technique is very advantageous, because it allows for a completely non-invasive method of accurately monitoring glucose level values with relatively simple sensors (e.g. electrodes) and hardware.

Additionally, blood glucose level may also be determined using an impedance-based technique, such as a resonant frequency-based method. An example of an impedance-based blood glucose measurement is described by Talary, et al., in "Non-Invasive Impedance based Continuous Glucose Monitoring System," published by IFMBE in 2007, the content of which is incorporated by reference herein in its entirety. This approach also only requires electrodes as a sensor.

The outputs from these two methods (e.g., ECG-based and BI-based) may be combined using a linear equation or other methods to get a highly accurate glucose level. This technique is also advantageous, as the accuracy of the readings may be further improved by combining these methods and outputting an even more accurate value using only electrodes touching a patient's skin. Thus, the entire system can provide precise blood glucose level readings from only electrodes functioning as sensors and voltage appliers.

Certain aspects and features of the present disclosure may also be used to monitor impedance of the body generally. Impedance is typically measured by passing a small alternating current between two or more electrodes connected to the skin. Thus, the measured impedance reflects contributions from more than a single electrode. Bioimpedance, or biological impedance or bioelectrical impedance, is defined as the ability of biological tissue to impede electric current. The main bioimpedance measurement approaches use either single-frequency signals or multiple-frequency signals (e.g., frequency-swept signals or broadband frequency spectrum signals).

Impedance monitoring has been shown to be useful for elimination of motion artifacts, such as disclosed by Romero et al., "Motion Artifact Reduction in Ambulatory ECG Monitoring: An Integrated System Approach," available at https://www.researchgate.net/publication/220906595_Motion_Artifact_Reduction_in_Ambula tory_ECG_Monitoring_An_Integrated_System_Approach, the content of which is incorporated herein by reference in its entirety. Furthermore, additional applications of bioimpedance monitoring are disclosed by Khalil et al., "The Theory and Fundamentals of Bioimpedance Analysis in Clinical Status Monitoring and Diagnosis of Diseases," published June 2014 and available at https://www.ncbi.nlm.nih.gov/pmc/articles/PMC4118362/, the content of which is incorporated herein by reference in its entirety.

In some cases, BI spectroscopy, or impedance spectroscopy, as disclosed herein, is a unique BI approach that differs in underlying basis from the single-frequency bioelectrical impedance analysis (SF-BIA) as it does not require the use of statistically derived, population-specific prediction equations to determine the injected current and filter the measured current. For instance, in some examples, the disclosed systems and methods apply voltage using a 1 kHz-200 MHz or 10 MHz-200 MHz frequency sweep electromagnetic field to perform impedance spectroscopy. Other frequencies and frequency ranges can be used.

The disclosed technology can be implemented in a smart patch, smartwatch, bracelet, ring, band, smart bra, smart clothing, digital stethoscope, Holter monitor or other device. For illustrative purposes, the ECG/BI measurement system described below is incorporated into a smart patch. The smart patch can be affixed to a user, such as the chest of the user, using adhesive. The smart patch can use its integrated sensors and electrodes to acquire physiological signals from direct contact with the user's skin. In some cases, non-contact measurements may also be acquired via optical sensing and electromagnetic signaling, among other methods.

BI data can be used to determine various physiological metrics, as well as other characteristics of the user, such as existing or predicted diseases and conditions. Examples of uses for BI data can include determining a volume of distribution of urea (UDV), determining glucose levels, determining hydration levels, determining body composition, determining glomerular filtration rate in non-diabetic patients, predict muscle mass and improving the estimation of glomerular filtration rate in non-diabetic patients suffering from chronic kidney disease, determine respiration (e.g., respiration can be derived from BI impedance modulation at high frequencies, such as averaged over a range 7 k-10 kHz, due to breathing), determining respiration rate variability, identifying or predicting cardiovascular-respiratory diseases (e.g., congestive heart failure (CHF) and obstructive sleep apnea (OSA) might be detected from respiratory feature extraction and anomaly detection), performing impedance plethysmography (e.g., for impedance cardiography (ICG) to determine cardiac output (CO), stroke volume (SV), and systolic time intervals). Other features can be extracted from BI data.

ECG data can be used to determine various physiological metrics, as well as other characteristics of the user, such as existing or predicted diseases and conditions. Examples of uses for ECG data can include determining the rate and/or rhythm of heartbeats, determining the size and position of the heart chambers, determining the presence of any damage to the heart's muscle cells or conduction system, assessing the functioning of implanted pacemakers, determining the effort from athletes while performing and training, performing biometric authentication (e.g., where ECG data from a wearable body sensor can be used as a uniquely identifiable biometric trait due to its unique identity properties, including user-specific deviations in ECG morphology and heart rate variability), enabling affective computing (e.g., via emotional recognition systems based on physiological signals, such as ECG, EDA and others, which can be used to adapt the wearable device and its applications to the users' affective/emotional state), performing physiology studies (e.g., ECG, among other metrics, can be used to determine the physiological state of a user by measuring mental stress levels, sleep apnea events, the intensity of physical activity, and the like), estimating respiratory signals (e.g., ECG-derived respiration (EDR) based on observing the beat-to-beat variations in the R peaks intervals from the ECG sensor and correlating those intervals to respiratory frequencies). Other features can be extracted from BI data.

These illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative embodiments but, like the illustrative embodiments, should not be used to limit the present disclosure. The elements included in the illustrations herein may not be drawn to scale.

FIG. 1 is a top view of a smart patch 100 employing an ECG/BI measurement system 102, according to certain aspects of the present disclosure. The smart patch 100 can include an electronics module 106 coupled to a patch substrate 104. The electronics module 106 can enclose the electronic circuitry and sensors for recording, storing, processing, and/or wirelessly transmitting (e.g., to a user device, such as a smartphone, or server over a communications network) a user's physiological health metrics. The electronics module 106 can contain a power supply, such as a battery. In some cases, the electronics module 106 includes a sealed housing, which can be a waterproof housing, a water-resistant housing, a dust-proof housing, or a housing sealed against other particles.

The electronics module 106 can be permanently coupled to the patch substrate 104, although that need not always be the case. In some cases, the electronics module 106 is releasably coupled to the patch substrate 104, such as to replace the patch substrate 104 with another patch substrate, to establish a physical connection for transferring data between the electronics module 106 and another device, or to recharge or otherwise provide power to the electronics module 106. In some cases, the entire smart patch 100 is disposable.

The patch substrate 104 of the smart patch 100 can have an exposed surface (e.g., the surface facing out of the page in FIG. 1 or the surface facing away from the user when the smart patch 100 is worn by a user) and a user-facing surface (e.g., the surface facing into the page in FIG. 1, or the surface facing towards the user when the smart patch 100 is worn by a user). A plurality of electrodes (e.g., hydrogel electrodes) is disposed at (e.g., on or in) the user-facing surface of the patch. Each electrode can thus be electrically couplable to the skin of a user when the user-facing surface is placed against the skin of the user. The plurality of electrodes can include at least one pair of electrodes that is shared for ECG and BI measurements, and optionally a second pair of electrodes, which may or may not be shared for ECG and BI measurements. Flexible conductors (e.g., flexible circuit traces) can electrically couple each electrode to the electrical circuitry within the electronics module 106, such as to a printed circuit board (PCB) within the electronics module 106. As used herein, the term "PCB" is generally used to refer to the main board of an ECG/BI measurement system, where appropriate. It is understood that a PCB can be implemented using one or more physical boards. The user-facing surface of the patch substrate 104 can also include an adhesive layer for securing the smart patch 100 against the skin of a user, which can secure each of the electrodes against the user's skin.

When the electrodes are positioned against the user's skin, electrical signals can be transferred between the user's skin and the circuitry in the electronics module 106. Such electrical signals can include signals received by the electronics module 106 for the purposes of ECG or BI measurements. In some cases, such electrical signals can also include signals transmitted from the electronics module 106 to the user's skin, such as for the purpose of current injection for certain BI measurements.

The patch substrate 104 can be designed with an ergonomic curved shape, as depicted in FIG. 1, although that need not always be the case. The patch substrate 104 can comprise any suitable shape, such as an hourglass shape, a rectangular shape, a circular shape, an oval shape, or the like. The patch substrate 104, other than the conductive and/or adhesive elements, can be made of a semi-rigid, water-resistant, non-electrically-conductive material (e.g., a semi-rigid water-resistant resin, plastic, polymer composite, or the like), such as polyurethane. Such materials can insulate the conductive elements enclosed inside the patch substrate 104 and are resistant to various types of corrosion and damage from continuous wear. The smart patch 100 may thus be worn continuously for extended periods of time (e.g., one or more days, such as on the order of ones or tens of days), such as at least fourteen days. After the smart patch 100 is removed, it can be replaced with another smart patch 100.

The ECG/BI measurement system 102 can include the electrodes of the patch substrate 104 and electronics within the electronics module 106 that are used for ECG and BI data acquisition using at least one shared pair of electrodes.

Figure 2:
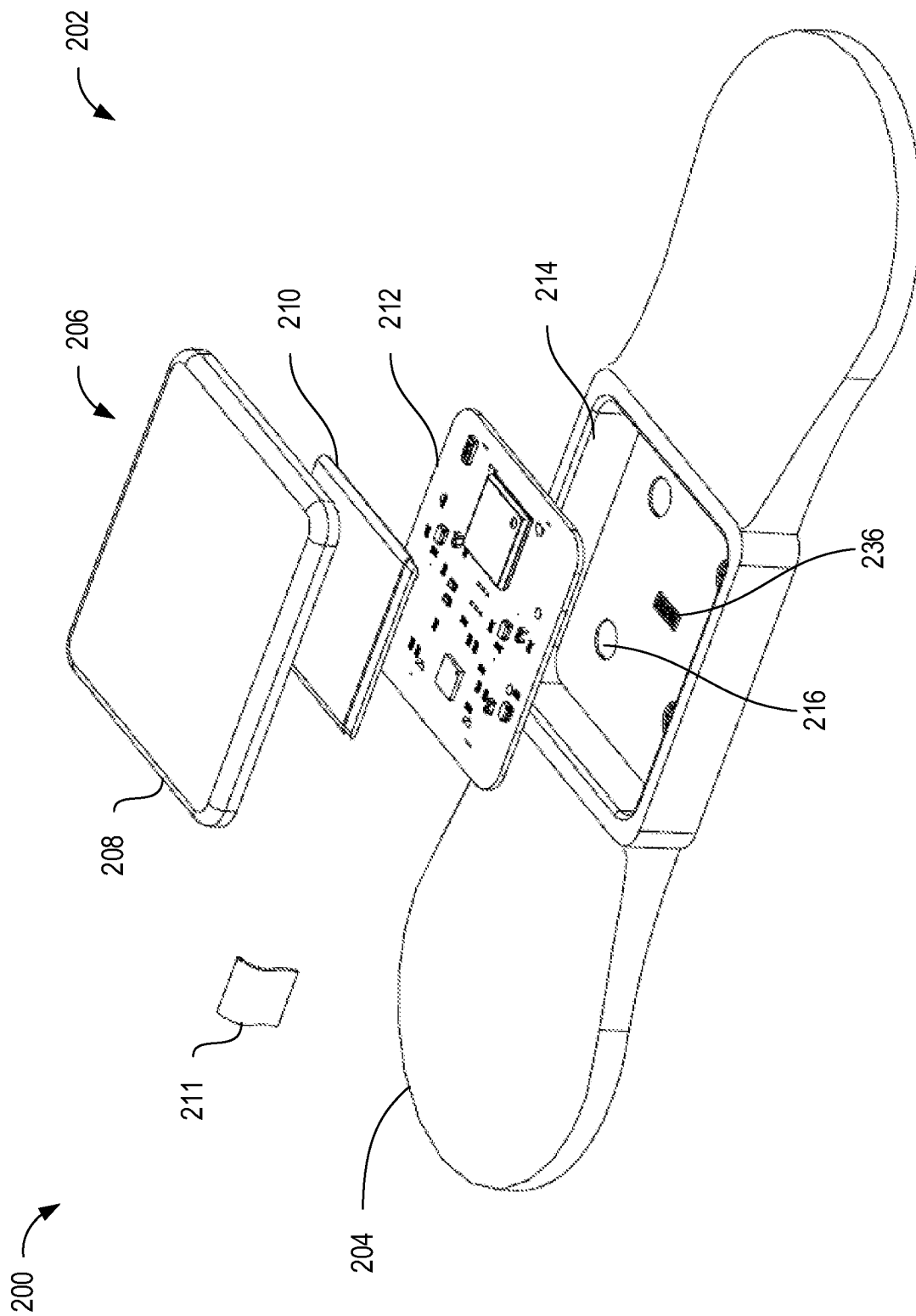
FIG. 2 is an exploded graphical projection of a smart patch employing an ECG/BI measurement system, according to certain aspects of the present disclosure.

FIG. 2 is an exploded graphical projection of a smart patch 200 employing an ECG/BI measurement system 202, according to certain aspects of the present disclosure. Smart patch 200 can be any suitable smart patch, such as smart patch 100 of FIG. 1. While a smart patch can include a removable electronics module in some cases, the smart patch 200 of FIG. 2 is depicted with a non-removable electronics module 206.

The electronics module 206 can include a top cover 208, a battery 210 (e.g., lithium-ion battery or the like), a PCB 212, and a base 214. The PCB 212 can contain various circuitry and components used to acquire ECG and BI data from a user. The battery 210 can be coupled to the PCB 212 in any suitable fashion, such as via a battery cable 211 (e.g., a thin, flexible cable).

As depicted in FIG. 2, the base 214 includes a set of electrode connectors 216 that interface with corresponding conductors extending from the PCB 212. Each electrode connector 216 can be electrically coupled to a corresponding electrode at the user-facing surface of the patch substrate 204, such as via flexible conductors. When the PCB 212 is installed in the base 214, the extending conductors of the PCB 212 can contact the electrode connectors 216, thus electrically coupling the PCB 212 to the electrodes at the user-facing surface of the patch. Electrode connectors 216 and corresponding conductors of the PCB 212 can take any suitable form, such as a plug-and-socket form or a pad-and-pin form. As depicted in FIG. 2, each electrode connector 216 is formed as a round pad of conductive material against which a corresponding conductor from the PCB 212 can be placed.

As depicted in FIG. 2, the smart patch 200 includes four electrode connectors 216. Four electrode connectors 216 can be used to connect the PCB 212 to two pairs of electrodes (e.g., four electrodes). In some alternative cases, the PCB 212 can be coupled to the electrodes without the use of any intermediate connectors (e.g., without the use of an electrode connector 216) between the PCB 212 and the flexible conductor. For example, the PCB 212 can be coupled directly to the flexible conductor or can be coupled to the flexible conductor via a non-connector conductor (e.g., a wire soldered to the flexible conductor and soldered to the PCB 212). However, the use of electrode connectors 216 can facilitate easy manufacturing of the smart patch 200, as well as facilitate easy removal of an electronics module in certain versions of a smart patch having a removable electronics module. In versions where the electronics module is removable, the patch substrate can include a receptacle for removably receiving the electronics module.

In some cases, the electronics module 206 can further include an optical sensor 236. As depicted in FIG. 2, the optical sensor 236 is embedded in the base 214 and is removably couplable to the PCB 212 via a pin connector (e.g., a multi-pin connector), although that need not always be the case. In some cases, an optical sensor can be coupled to a PCB, such as by being soldered to the PCB, and the base can include an opening that optically exposes the optical sensor to the skin of the user when the PCB is installed in the electronics module and the smart patch is worn by a user. In such cases, the opening can be optionally covered by a window that is transparent or sufficiently translucent to the wavelengths used by the optical sensor.

The optical sensor 236 can be used for photoplethysmography (PPG) sensing. In such cases, the optical sensor 236 can include one or more light emitting diodes (LEDs) and one or more photodiodes, with LEDs emitting light and the photodiodes detecting light. Examples of suitable LEDs include green LEDs, red LEDs, infrared (IR) LEDs, blue LEDs, or yellow LEDs, although other LEDs can be used. When more than one light emitter is integrated, the plurality can include emitters with the same or different wavelengths. The optical sensor 236 for PPG measurements may include one or more light emitters and one or more photodetectors. The light emitters and photodetectors may also be arranged in any suitable configuration at the bottom of the optical sensor 236. The optical sensor 236 can be positioned in the base 214 and can access the skin of the user directly via the user-facing surface of the patch substrate 204; the optical sensor 236 can draw power from and exchange data with the PCB 212 via an electrical connector. Any suitable electrical connector can be used, such as a pin connector, a multi-pin connector, a header connector, a plug connector, and the like. The electrical connector can include a first end coupled to the optical sensor 236 that electrically couples to a second end coupled to the PCB 212. In some cases, an optical sensor can be positioned on the bottom of the PCB instead and is able to access the skin of the user through a window of the base. When used for PPG sensing, the optical sensor 236 can detect the heart rate of the user, the blood oxygenation of the user among other health metrics, and/or can enhance the accuracy of the acquired ECG data. Other sensors may be integrated into the smart patch 200 for capturing physiological signals.

The ECG/BI measurement system 202 can include the electrodes of the patch substrate 204 and electronics within the electronics module 206 that are used for ECG and BI data acquisition using at least one shared pair of electrodes.

Figure 3:
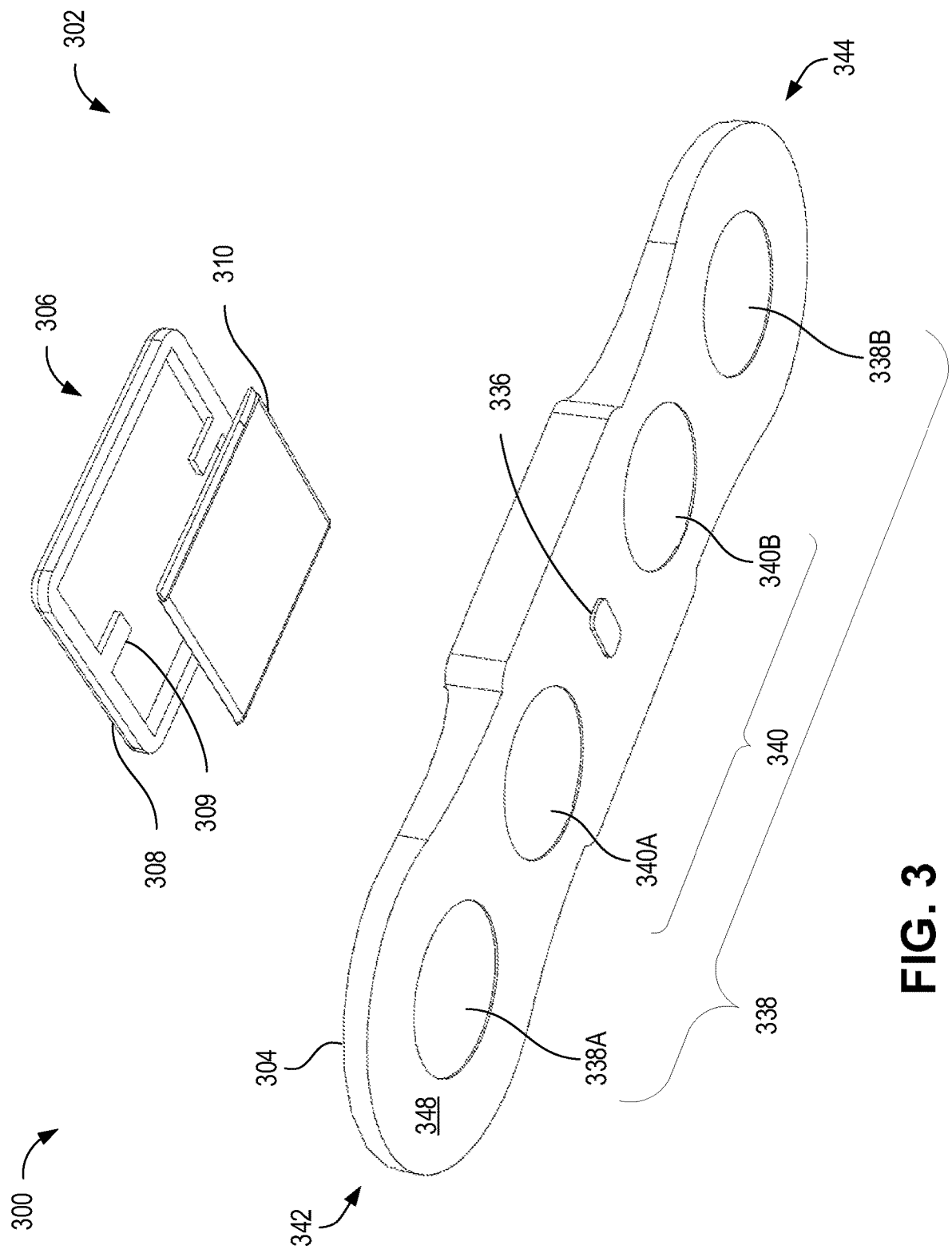
FIG. 3 is a partially exploded graphical projection of an underside of a smart patch employing an ECG/BI measurement system, according to certain aspects of the present disclosure.

FIG. 3 is a partially exploded graphical projection of an underside of a smart patch 300 employing an ECG/BI measurement system, according to certain aspects of the present disclosure. Smart patch 300 can be any suitable smart patch, such as smart patch 100 of FIG. 1.

For illustrative purposes, the battery 310 of the electronics module 306 and the top cover 308 are shown in exploded view. In some cases, the battery 310 can be attached to the top cover 308, such as using tabs 309, adhesives, or other suitable techniques. By being attached to the top cover 308, battery 310 can be held spaced apart from the PCB, thus providing an air gap between the battery 310 and the PCB. The air gap can prevent overheating of electrical components within the electronics module 306.

In some cases, battery 310 can be rechargeable or replaceable. In some cases, the top cover 308 can be opened to access the battery 310 for recharging or replacement. In some cases, other techniques can be used to recharge the battery 310, such as via inductive charging and/or an exposed port or exposed connectors on the smart patch 300. In some cases, however, the battery 310 is disposable, along with the rest of the smart patch 300.

The user-facing surface 348 of the patch substrate 304 is shown. Four electrodes 338A, 338B, 340A, 340B are disposed at the user-facing surface 348 such that placement of the user-facing surface 348 against the skin of a user individually electrically couples each of the four electrodes 338A, 338B, 340A, 340B to the user's skin. In some cases, each of the four electrodes 338A, 338B, 340A, 340B can be individually addressed. In some cases, all of the electrodes 338A, 338B, 340A, 340B are aligned along a line (e.g., are collinear), such as depicted in FIG. 3. In such cases, electrodes 338A, 340A may be positioned on a first arm 342 of the patch substrate 304 and electrodes 338B, 340B may be positioned on an opposite, second arm 344 of the patch substrate 304. While the patch substrate 304 is depicted as having a first arm 342 and a second arm 344, other shapes can be used to achieve the desired positioning of electrodes 338A, 338B, 340A, 340B. In some cases, electrodes 338A, 338B, 340A, 340B can be positioned on extensions, sections, or other regions of a patch substrate 304 having any suitable shape (e.g., rectangular, circular, oval, and the like).

In some cases, outer electrodes 338A, 338B can be used as an outer pair of electrodes (referred to as outer electrode pair 338), and inner electrodes 340A, 340B can be used as an inner pair of electrodes (referred to as inner electrode pair 340). In some cases, the electrodes 338A, 338B, 340A, 340B can be symmetrically arranged in a linear array. For example, a centerpoint between the inner electrodes 340A, 340B can be the same as the centerpoint between the outer electrodes 338A, 338B. Either of the inner electrode pair 340 or the outer electrode pair 338 can be used as a shared pair of electrodes for both ECG and BI measurement. In some cases, certain smart patches include only a single pair of electrodes (e.g., only electrodes 340A, 340B).

Electrical signals can be transmitted and/or received via any suitable electrode 338A, 338B, 340A, 340B. In some cases, the outer electrode pair 338 can be used for the injection of electrical current into the skin of the user for BI measurement purposes. In some cases, inner electrode pair 340 can be used for measuring electrical signals from the skin of the user to acquire ECG data and BI data. In some cases, however, the outer electrode pair 338 and inner electrode pair 340 can be used otherwise.

In the smart patch 300 depicted in FIG. 3, an optical sensor window 336 is depicted in the user-facing surface 348, providing an opening through which an optical sensor (e.g., an optical sensor 236 embedded in the base 214 of the patch substrate 304 or an optical sensor coupled to the PCB) can access the user's skin for optical measurements (e.g., PPG measurements).

In some cases, the user-facing surface 348 can be covered with or can include an adhesive layer (e.g., a biocompatible and preferably breathable adhesive layer) and/or a gel layer (e.g., conductive hydrogel layer). In some cases, each of the electrodes 338A, 338B, 340A, 340B can be covered with a conductive gel layer, the optical sensor window 336 can be uncovered (e.g., without adhesive), and the remainder of the user-facing surface 348 can be covered with an adhesive layer. When the smart patch 300 is applied to the skin of a user, the conductive gel layer can provide electrical conductivity between the skin of the user and the electrodes 338A, 338B, 340A, 340B. In some cases, a peel-away layer can cover any adhesive and/or gel layers for protection prior to the attachment of the smart patch 300 to the skin of a user.

Figure 4:
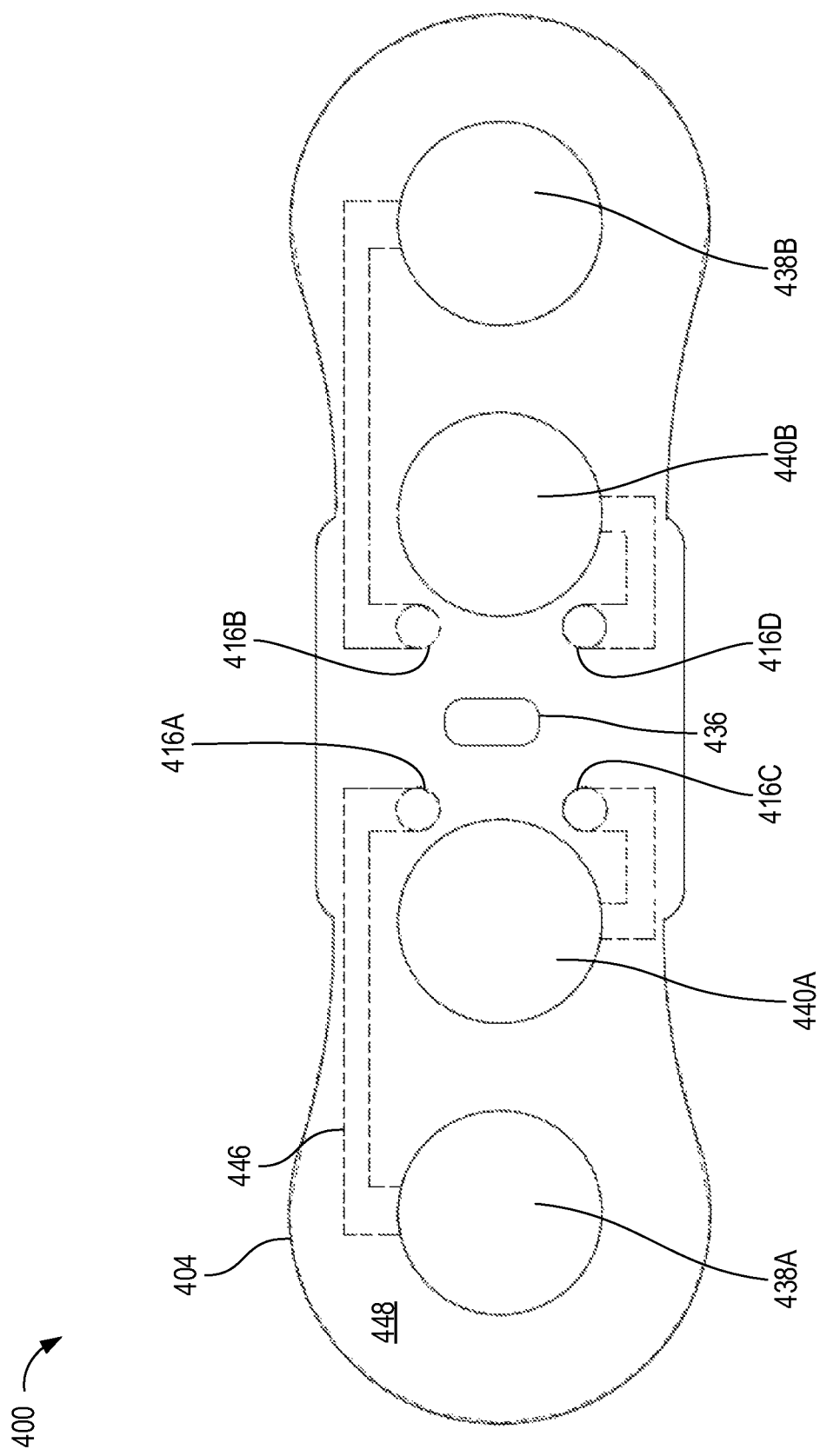
FIG. 4 is a bottom view of a smart patch employing an ECG/BI measurement system, according to certain aspects of the present disclosure.

FIG. 4 is a bottom view of a smart patch 400 employing an ECG/BI measurement system, according to certain aspects of the present disclosure. Smart patch 400 can be any suitable smart patch, such as smart patch 100 of FIG. 1. The user-facing surface 448 of the patch substrate 404 is shown, including its electrodes 438A, 438B, 440A, 440B and a sensor window 436. For illustrative purposes, flexible conductors 446 are depicted coupling each of the electrodes 438A, 438B, 440A, 440B to respective electrode connectors 416A, 416B, 416C, 416D, which can be used to electrically couple the electrodes 438A, 438B, 440A, 440B to a PCB.

In some cases, the smart patch may include only two electrodes or may include more than four electrodes. In some cases, each electrode 438A, 438B, 440A, 440B can be a wet electrode (e.g., an electrode coated in a conductive gel, covered with a saline solution), a dry electrode (e.g., a silver-silver chloride electrode), a semi-dry electrode (e.g., an electrode with a reservoir of electrolyte releasable to the electrode-skin interface). In some cases, ceramic-based or other types of electrodes can be used.

Sensor window 436 can permit one or more sensors (e.g., non-contact sensors) to access the skin of the user. In some cases, the one or more sensors can include environmental sensors (e.g., a temperature and/or humidity sensor), optical sensors (e.g., PPG sensors), or electrodermal activity (EDA) sensors (e.g., galvanic skin response sensors). When only non-contact sensors are used, the sensor window 436 can be covered by a window material (e.g., plastic, sapphire crystal, mineral crystal, plexiglass, hesalite crystal, glass, or the like) that is sufficiently translucent or transparent to the wavelengths used by the non-contact sensor. Such a window material can prevent liquids or particles from damaging the sensor(s) and/or other components within the electronics module. The sensor window 436 can be made in any suitable shape. In some cases, multiple sensor windows can be used in any suitable arrangement.

In some cases, the user-facing surface 448, and any adhesive layers, gel layers, and/or other layers, can be sweat resistant, including being made from a low-moisture-absorbance material. In some cases, tabs can be placed at each end of the adhesive layer for easy removal of the smart patch 400 from the skin of a user.

Figure 5:
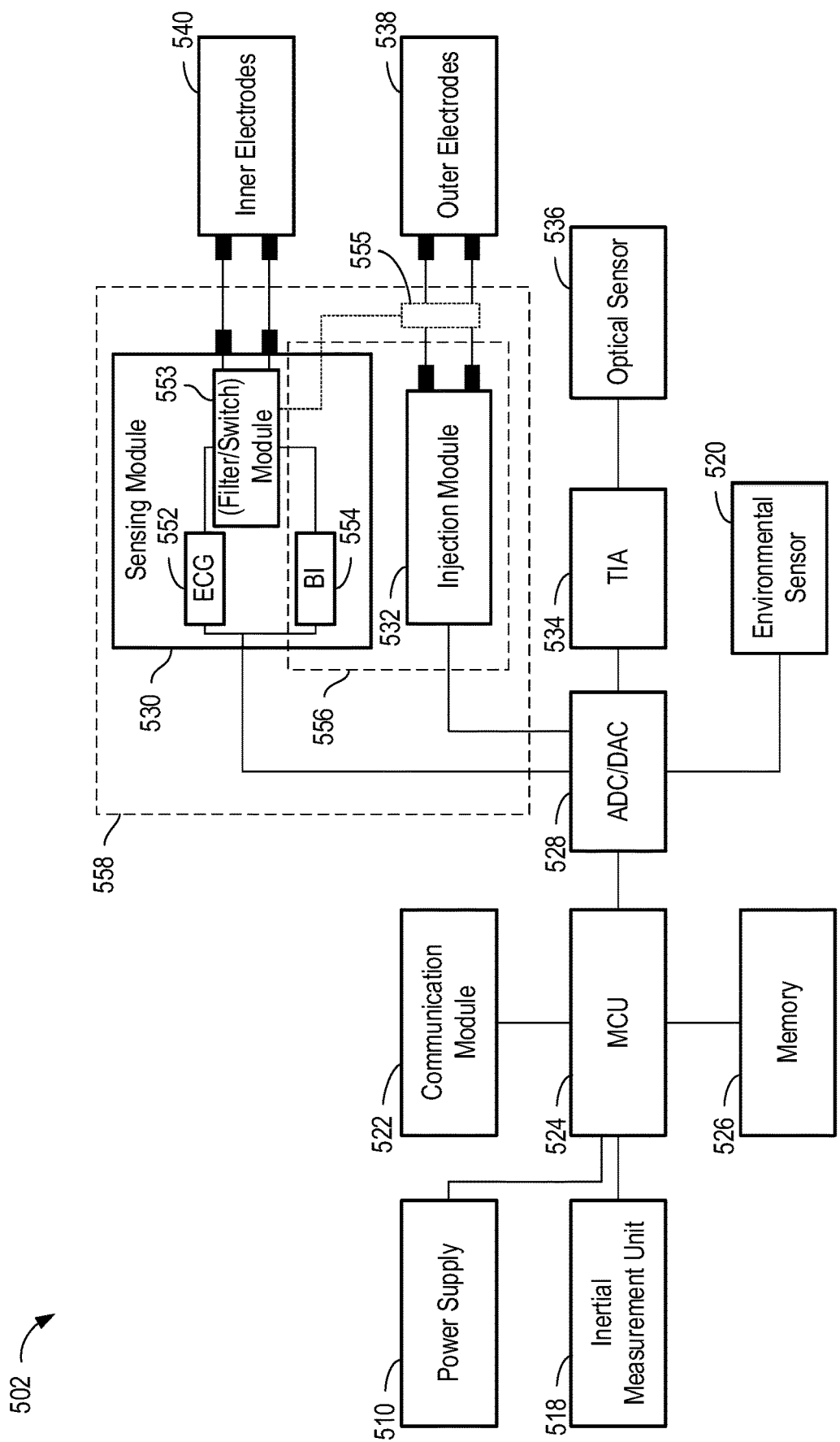
FIG. 5 is a schematic diagram of an example ECG/BI measurement system for extracting ECG and BI data from a signal, according to certain aspects of the present disclosure.

FIG. 5 is a schematic diagram of an example ECG/BI measurement system 502 for extracting ECG and BI data from a signal, according to certain aspects of the present disclosure. The ECG/BI measurement system 502 can be any suitable ECG/BI measurement system incorporated into any suitable device, such as ECG/BI measurement system 102 incorporated into smart patch 100 of FIG. 1. The ECG/BI measurement system 502 can include a number of components that act as a control system to enable certain aspects and features of the present disclosure, such as the simultaneous or sequential measurement of ECG data and BI data.

The ECG/BI measurement system 502 can include a microcontroller (MCU) 524, memory 526, one or more sensors (e.g., inertial measurement unit (IMU) 518 and environmental sensor 520), a communication module 522, and a power supply 510 (e.g., one or more batteries). In some cases, an ECG/BI measurement system 502 can further include one or more user interfaces coupled to the MCU 524, such as user inputs (e.g., buttons or other sensors) and output devices (e.g., a computer display; a light emitting diode (LED); a speaker; a haptic actuator, such as an eccentric rotating mass motor, a linear resonant actuator, a piezoelectric actuator, etc.; and the like).

MCU 524 can be any suitable processing unit (e.g., processor) or controller. Memory 526 can be any suitable memory or combination of memory modules. Memory 526 can include a cache, a flash memory, a read only memory (ROM), a random access memory (RAM), or any combination thereof. Memory 526 can be used to store collected data (e.g., health signals), device settings, user settings, machine-readable instructions for performing certain aspects of the present disclosure, or other information.

In some cases, the ECG/BI measurement system 502 can include one or more sensors, such as an IMU 518 and an environmental sensor 520. The IMU 518 can include an accelerometer, gyroscope, magnetometer, or any combination thereof. In some cases, other inertial and/or location sensors can be implemented as part of the IMU 518 or used in addition to the IMU 518. In some cases, the environmental sensor 520 can be positioned to acquire data from an ambient environment (e.g., an ambient environment surrounding the wearable device in which the ECG/BI measurement system 502 is implemented and/or surrounding a user wearing the wearable device. In some cases, the environmental sensor 520 can be positioned adjacent to the skin of the user when the ECG/BI measurement system 502 is being worn by the user, such as to acquire temperature and/or humidity data associated with the skin of the user. In some cases, multiple environmental sensors 520 can be used.

Power supply 510 can include one or more batteries or other suitable power sources. Such batteries can be rechargeable, although that need not always be the case. In some cases, the power supply 510 can include a charging module to recharge the rechargeable battery. The charging module can receive power from an induction coil, electrical contacts, or any other suitable mechanism. In some cases, when electrical contacts are used to power the charging module, the electrical contacts can couple through electrodes of the inner electrodes 540 or outer electrodes 538 or through electrical connectors that would otherwise connect to such inner electrodes 540 or outer electrodes 538.

The communication module 522 can support wired or wireless communication technologies. For example, the communication module 522 can be configured to establish wireless connections using a generic radiofrequency (RF) signal and/or one or more wireless standards, such as Bluetooth (e.g., Bluetooth Low Energy), Near Field Connection (NFC), WiFi, or a cellular system (e.g., 3G, 4G, 5G, and the like). Communication module 522 can facilitate establishing a connection between the MCU 524 and an external device, such as a user device (e.g., smartphone, smartwatch, computer, tablet, and the like) or a server accessible via a communication network (e.g., a local area network, a personal area network, a wide area network, a mobile network, a cloud network, or the Internet).

An analog-to-digital converter and/or digital-to-analog converter (ADC/DAC) module 528 can be coupled to the MCU 524 to send and/or receive signals. For example, signals from an environmental sensor 520 may pass through the ADC/DAC module 528 to be converted into a digital signal that is further processed by the MCU 524. In some cases, the ADC/DAC module 528 can be implemented within the MCU 524. In some cases, an individual ADC/DAC module can be incorporated into various other modules (e.g., IMU 518 may include its own ADC/DAC module for providing digital signals to the MCU 524).

An optical sensor array 536, having one or more optical sensors, can be coupled to the MCU 524 via the ADC/DAC module 528 and a transimpedance amplifier (TIA) 534. The TIA 534 can convert current to voltage when emitting a signal and can convert voltage to current when receiving a signal.

Inner electrodes 540 and outer electrodes 538 can be coupled to various circuit elements for effecting ECG measurement and BI measurement. ECG measurements and BI measurements can be collected simultaneously or nearly simultaneously using different schemes. In a first scheme, the ECG measurements and BI measurements can be collected simultaneously as a single signal that is then filtered to extract an ECG-related part and a BI-related part. In a second scheme, the ECG measurements and BI measurements can be collected using time-differentiated sampling, in which the sensed signal for the ECG measurements is received before or after the sensed signal for the BI measurements. In other words, a single set of electrodes can be switched between ECG circuitry 552 and BI circuitry 554.

As depicted in FIG. 5, outer electrodes 538 are used for current injection and inner electrodes 540 are used for sensing, although this need not always be the case. In some cases, the roles of the electrode pairs can be reversed. In some cases, a pair of electrodes can be switched between injecting current and sensing (e.g., sensing ECG). In some cases, only a single pair of electrodes is used.

The inner electrodes 540 and outer electrodes 538 can be coupled to the MCU 524 via a ECG/BI interface module 558. The ECG/BI interface module 558 can include submodules, components, and other elements that are used to acquire ECG signals and BI signals from the user's skin. ECG/BI interface module 558 can include a sensing module 530 and an injection module 532.

In the example of FIG. 5, outer electrodes 538 are coupled to an injection module 532 and inner electrodes 540 are coupled to a sensing module 530. While described as separate modules, the sensing module 530 and injection module 532 are not necessarily separate and can include common components. For example, a BI-measurement subsystem 556 can include both the injection module 532 and the BI circuitry 554 of the sensing module 530.

The sensing module 530 can receive signals from the inner electrodes 540 and output one or more data signals to the MCU 524 via the ADC/DAC module 528. The one or more data signals can include ECG data signals, BI data signals, or combined ECG/BI data signals.

The ECG/BI measurement system 502 can be implemented in different schemes. For example, in some implementation schemes, filter/switch module 553 can be a filtering module used to filter incoming data to either the ECG circuitry 552 or BI circuitry 554. In other implementation schemes, filter/switch module 553 can be a switching module used to switch incoming data from being directed to either the ECG circuitry 552 or the BI circuitry 554. Therefore, for illustrative purposes, module 553 is depicted as a "filter/switch module," although in any given implementation it may be a filtering module or a switching module.

In a first scheme (e.g., a simultaneous scheme), module 553 is a filter module that separates an incoming signal into an ECG-related part and a BI-related part. The ECG-related part is sent to ECG circuitry 552 that further filters and/or otherwise processes the ECG-related part of the incoming signal into an ECG signal. The BI-related part is sent to BI circuitry 554 that further filters, extracts features and/or parameters and/or otherwise processes the BI-related part of the incoming signal into a BI signal.

In a second scheme (e.g., a sequential scheme), module 553 is a switching module that switches the inner electrodes 540 between the ECG circuitry 552 and the BI circuitry 554. The switching module (e.g., module 553) can be triggered manually, automatically by a triggering event, or automatically by a clock signal. The switching module can be a controllable switch.

In some cases, when the switching module (e.g., module 553) is triggered to switch between directing the signals from the inner electrodes 540 to the ECG circuitry 552 and directing the signals to the BI circuitry 554, the outer electrodes 538 can be automatically disconnected from the injection module 532 by optional switching module 555. In some cases, optional switching module 555 can be part of module 553, and this disconnection of the outer electrodes 538 can occur by this single module 553. In some cases, optional switching module 555 can be separate from module 553 and can be controlled by module 553 or in tandem with module 553, thus disconnecting outer electrodes 538 as module 553 switches.

In some cases, instead of or in addition to disconnecting the outer electrodes 538 from the injection module 532, the outer electrodes 538 can also be temporarily coupled to ECG circuitry 552 or a separate piece of ECG circuitry, such as to generate a second ECG data signal measured between the outer electrodes 538. This coupling occurs when the switching module (e.g., module 553) switches to coupling the inner electrodes 540 with ECG circuitry 552, thus permitting two ECG signals to be acquired when BI is not being measured. When the switching module switches back to coupling the inner electrodes 540 with the BI circuitry 554, the outer electrodes 538 can be disconnected from any ECG circuitry and, if previously disconnected from the injection module 532 during ECG measurement, can be connected to the injection module 532. Thus, when BI is being measured, the inner electrodes 540 can be coupled to BI circuitry 554 while the injection module 532 provides an injection current to the outer electrodes 538.

Whenever BI is being measured, in any scheme, the injection module 532 can supply the necessary electrical signals (e.g., injection current) used for BI measurement. This injection current supplied to the skin of the user via outer electrodes 538 can include a current supplied at a single frequency or a current supplied at multiple frequencies. In some cases, supplying a current at multiple frequencies can include providing the injection current as multiple subsequent currents at different frequencies (e.g., a sweeping injection current). In some cases, supplying a current at multiple frequencies can include providing the injection current as a single current comprising multiple components having different frequencies (e.g., a broadband injection current).

Each of the modules described in ECG/BI measurement system 502 can include various sub-modules, components, or other elements for implementing the functionality of the module.

In an example, the ECG/BI interface module 558, can include a multiplexer and demultiplexer. The multiplexer and demultiplexer can be used to select among the electrodes involved in injecting current into the tissue and measuring the resulting voltage. Additionally, a high-pass filter can remove the direct current (DC) offset at the instrumentation amplifier's (IA) output when recording bio-impedance. In some cases, such a filter can be incorporated into the filter/switch module 553.

In any scheme (e.g., simultaneous measurement or sequential measurement), the ECG/BI interface module 558 can include one or more analog front-ends (AFEs) and one or more filters. In some cases, each of the ECG circuitry 552 and BI circuitry 554 can have their own respective AFE and filters. As described elsewhere herein, in some cases, instead of a central ADC/DAC module 528 or as part of the ADC/DAC module 528, each of the ECG circuitry 552 and BI circuitry 554 can include respective ADC/DAC modules.

In some cases, one or more circuit breakers can be used to protect circuits within the ECG/BI measurement system 502 from excess current. The MCU 524 can be used to set and/or adjust settings of the one or more circuit breakers.

In some cases, additional modules can be integrated into the ECG/BI measurement system 502 (e.g., internal modules) or be coupled to the ECG/BI measurement system 502 (e.g., external modules) via a wired or wireless connection. These internal or external modules can include additional sensors (e.g., biosensors), additional processing circuitry, or other suitable components.

In some cases, certain aspects of the ECG/BI measurement system 502 can be implemented as an application specific integrated circuit (ASIC).

Figure 6:
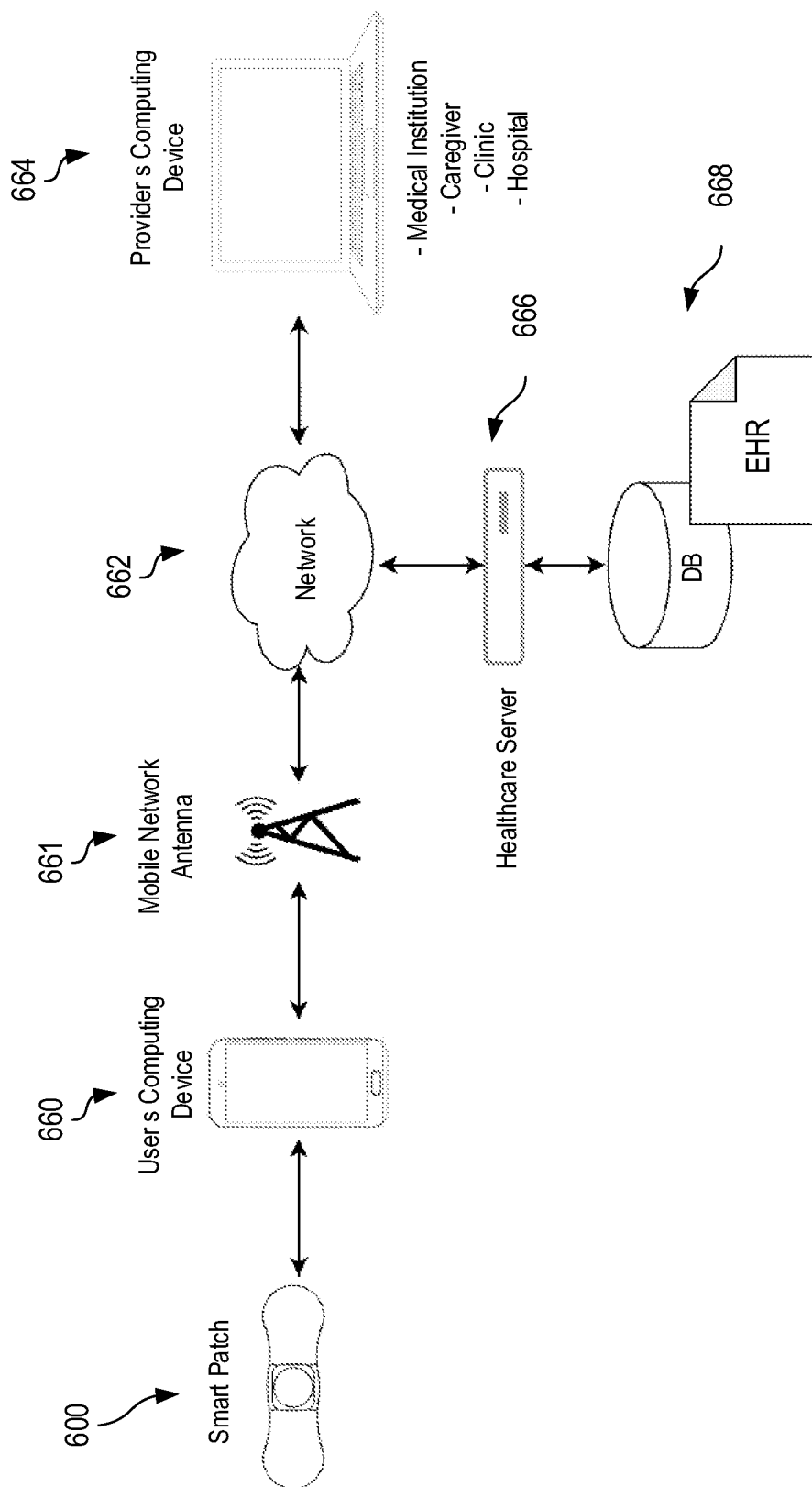
FIG. 6 is a schematic diagram depicting a smart patch connecting to a network via a computing device in a computing environment, according to certain aspects of the present disclosure.

FIG. 6 is a schematic diagram depicting a smart patch 600 connecting to a network 662 via a computing device 660 in a computing environment, according to certain aspects of the present disclosure. Smart patch 600 can be any suitable smart patch, such as smart patch 100 of FIG. 1.

The smart patch 600 can be communicatively coupled to a computing device 660, such as a user's computing device (e.g., smartphone, smartwatch, tablet, laptop, computer, or the like). The computing device 660 uses a communication interface to wirelessly send and/or receive data. The smart patch's communication interface may support bi-directional wireless data transfer. In some cases, the communication interface may be utilized just to send data whereas in other embodiments, besides transmitting data, the communication interface may also receive data remotely (e.g., updates to OS, firmware, security keys, ML models, algorithms, settings, commands to activate specific sensors that are not always on, and the like).

The diagram of FIG. 6 outlines a communications data flow for how information from the smart patch 600 can be transmitted to a healthcare server 666 and then stored in a patient's electronic health record (EHR) 668 for access by a clinician. The smart patch 600 can be attached to the chest area of the user and is configured to capture data (e.g., ECG data and BI data).

A computing device (e.g. a smartphone) 660 is paired with the smart patch 600 using NFC, BLE, or another suitable protocol. The computing device 660 can communicate to the network 662 via a connection to a mobile network antenna 661, although the computing device 660 can communicate with network 662 using other communication protocols, such as WiFi, BLE, and the like. As long as the smart patch 600 and the smartphone are wirelessly connected, all of the sensor data from the smart patch 600 can be streamed to the mobile device. Using a compatible mobile application installed on the smartphone, the user is able to see and manage their health metrics.

The smartphone application can securely transmit the data captured and/or generated by the smart patch over a network 662 (e.g., a LAN, PAN, WAN, mobile network, and/or the Internet) to a healthcare server 666. The data is then stored in the user's Electronic Health Record (EHR) 668 within a database system. The user's EHR 668 may contain other health and personal information not acquired from the smart patch 600 (e.g., physician notes from clinic visits, information about prescribed medications and doses, lab reports, diagnostic imaging reports, vaccination records, family medical history, genetic information, microbiome analysis, and the like).

The healthcare server 666 can include a medical knowledge graph learned algorithmically from EHRs 668 and a corpus of medical information that includes scientific papers published in academic journals, textbooks, manuals, public health data, and other data sources. The medical knowledge graph can learn relationships between diseases and symptoms across all these sources, which can be leveraged by the AI engine to generate inferences about the user's health state and make predictions about the user's health trajectory. These predictions can serve as a diagnostic tool for clinicians to make more timely decisions about patient care.

The medical knowledge graph can assume a bipartite graph, in which facts are represented as relations (edges) between entities (nodes). Resource Description Framework (RDF) is a common way of representing knowledge graphs. RDF defines relationships in the form of triplets comprising a head entity, relation, and tail entity (h, r, t). The medical knowledge graph is clinically useful in understanding the complex relationships between physiological data, symptoms, diseases, biochemistry, pharmacology, genomics, environmental data and other dimensions. The medical knowledge graph can be used to find correlations and provide automated recommendations for clinicians while treating patients. The medical knowledge graph may be a system of interacting and interlinked information networks. The content of the medical knowledge graph can also assume a multipartite graph structure that can provide very specific insights and recommendations to clinicians/researchers.

The healthcare server 666 can include an AI engine that provides predictive insights on patient conditions. The AI engine continually processes the user's EHR 668, including the data acquired from the smart patch 600, using AI/machine learning algorithms. The AI engine uses the medical knowledge graph to identify anomalies in the user's EHR 668, generate inferences about the user's health state, and make predictions about the user's health trajectory.

The AI engine uses a library of algorithms for generating predictions/inferences based on structured and unstructured medical data in the EHR 668 and medical knowledge graph. A wide range of ML approaches such as CNN (Convolutional Neural Networks), RNN (Recurrent Neural Networks), AutoEncoders, Deep Learning, DanQ, etc. can be used individually or in combination for processing EHR 668 and knowledge graph data. Trained models can enable high-accuracy detection of health conditions/states with minimal errors. These generated predictions/insights generated by the AI engine can support clinicians in their decision making and allow them to deliver more timely and accurate treatment by providing access to predictive insights, relevant patient information, and pertinent medical knowledge related to the patient's condition.

The healthcare server 666 can triage predictions from the AI engine using a scoring system which determines how urgently the patient may need healthcare provider attention (e.g., emergency condition or lower priority situation). The health inferences, together with the triage scores, may be used by the healthcare server 666 to automatically initiate a command to the smart patch 600 over the network 662 to update settings (e.g., sensor sampling rates) or issue commands (e.g., activate a specific sensor for a specified duration for continuous sampling in order to collect additional data or switch to ECG-only or BI-only monitoring for a duration of time).

The triage scores can also be used by the healthcare server 666 to provide notifications about a user's health state to a provider's computing device 664 (e.g., smartphone, tablet, computer, and the like). These notifications, along with the triage score, allow the physician to address the highest priority cases requiring urgent attention first. For example, a physician may receive a notification indicating that a user is suffering from tachycardia based on the ECG data, which may require immediate attention. The physician can then access real-time data from the user's smart patch 600 through the healthcare server 666. The physician can view a dashboard that shows the patient's real-time vitals. Since the patch functions to provide ECG measurements, BI measurements, and any other measurements associated with additional sensors of the patch, the physician can access and evaluate any of these measurements along with the patient's complete EHR.

The provider's computing device 664 can be associated with a medical institution, a caregiver (e.g., a physician, a nurse, an assistant, a family member, and the like), a clinic, a hospital, or other provider or collection of providers.

Through an application or web interface on the provider's computing device 664, the physician may also directly communicate with the smart patch 600 to update settings (e.g., sensor sampling rates) or issue commands (e.g., to activate a specific sensor for a specified duration if it is not continuously sampling data by default or to switch to ECG-only or BI-only monitoring for a duration of time).

In other cases, the physician may issue a command to the smart patch 600 through the healthcare server 666 that instructs the smart patch 600 to complete an invasive test using integrated microneedles and a lab-on-chip assembly. In some cases, the physician may issue a command to the smart patch 600 to initiate treatment using onboard medicines, such as via transdermal drug delivery. In some cases, transdermal drug delivery can be implemented by integrating a microfluidic architecture with microneedles that enable fluid management for transdermal treatment delivery.

These examples highlight the ability for the smart patch 600 to bi-directionally communicate with other devices over a network 662. The smart patch 600 can employ end-to-end data encryption to secure all communication with any other device (smartphone, healthcare server, provider's computing device, and the like).

Figure 7:
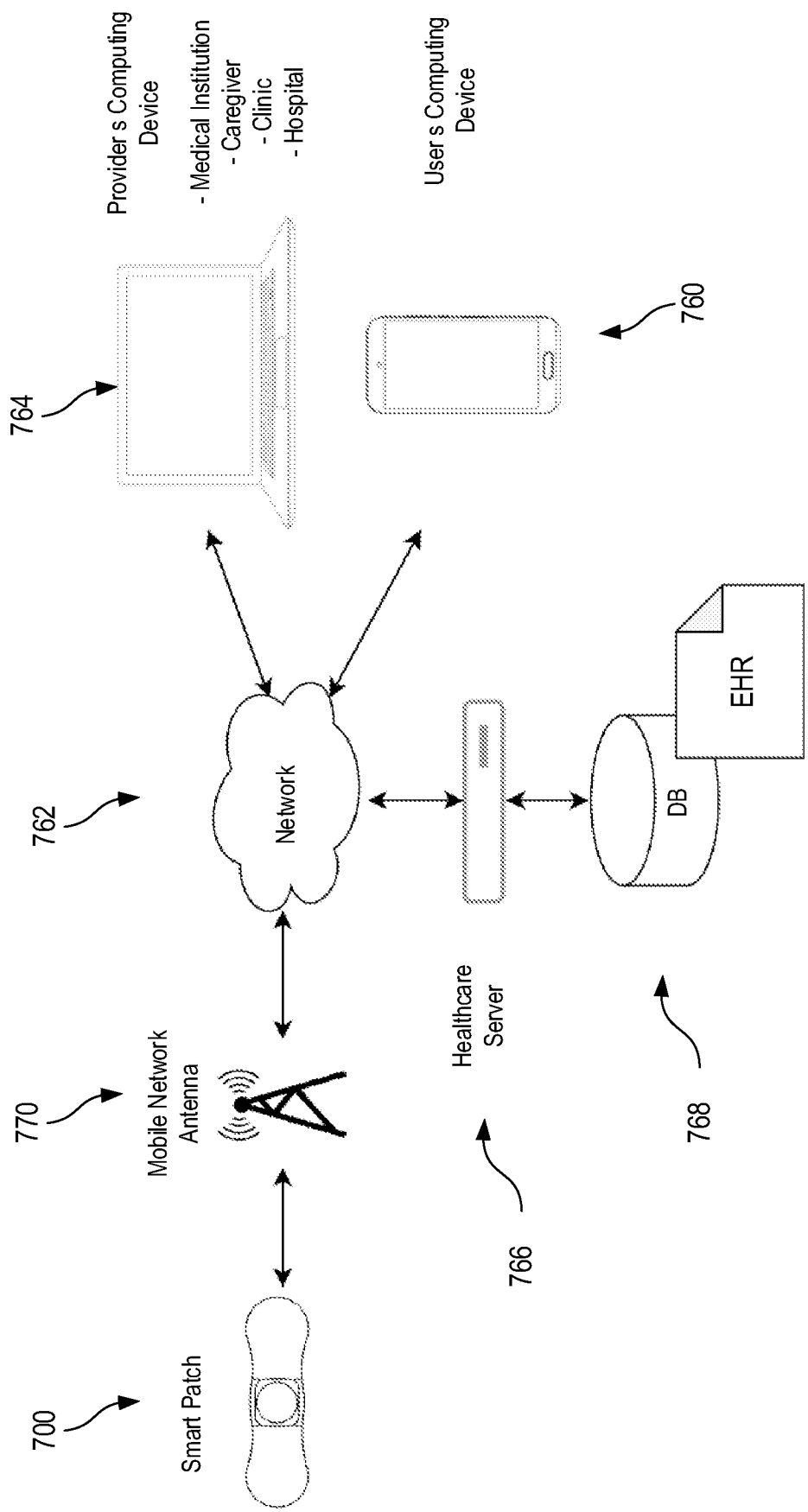
FIG. 7 is a schematic diagram depicting a smart patch connecting directly to a network in a computing environment, according to certain aspects of the present disclosure.

FIG. 7 is a schematic diagram depicting a smart patch 700 connecting directly to a network 762 in a computing environment, according to certain aspects of the present disclosure. Smart patch 700 can be any suitable smart patch, such as smart patch 100 of FIG. 1.

In some cases, smart patch 700 can connect directly to a network 762 via a mobile network antenna 770, using the smart patch's 700 internal mobile network radio and antenna. This direct connection allows the smart patch 700 to continuously stream sensor data to a healthcare server 766 for storage in the user's EHR 768 contained in a database system. The integrated mobile network radio and antenna in the electronics module obviates the need for the smart patch 700 to communicate with the healthcare server 766 through computing device 760 (e.g., a user's smartphone) or other wireless computing device as described with reference to FIG. 6.

In FIG. 7, the provider's computing device 764 can be used similarly to provider's computing device 664 of FIG. 6.

In FIG. 7, the user's computing device 760 can include an accompanying mobile health application installed which allows the user to securely access and/or synchronize their EHR 768 from the healthcare server.

The mobile health application can allow patients to aggregate their health records from multiple institutions alongside their patch-generated data, creating a more holistic view of their health. The mobile health application can leverage OAuth 2.0, which allows users to authenticate with other health provider systems once and create an enduring connection to their respective EHR 768. The mobile health application can periodically connect to the EHR 768 to pull in any new health records and notify the user when new records are available. The connection between the various distributed EHRs 768 and a user's mobile health application can utilize FHIR (Fast Healthcare Interoperability Resources) standard APIs as defined by the Argonaut Project. FHIR allows the mobile health application to aggregate health records from different providers in a standardized way for secure viewing and storage on the user's smartphone. All health data can be protected by an encrypted, direct connection when moving data between the smartphone and EHR provider APIs.

An API for the mobile health application could allow developers of fitness and health apps for smartphones and smart watches to access user data on the mobile health application in order to create a central data store for user fitness/health data.

All health data stored on the smartphone and accessible via the mobile health application can be encrypted and further protected by application-level and device-level authentication (e.g., password, PIN, face authentication, fingerprint authentication, voice authentication, and the like).

The mobile health application may show a real-time dashboard of patient vitals being captured from the smart patch 700, EHRs 768 at multiple providers (with information related to allergies, conditions, immunizations, lab results, diagnostic imaging reports, medications, procedures, vitals, wellness summaries, genetic information, microbiome analysis, etc.), cross-patient benchmarks, personalized recommendations (nutrition, fitness regime, mental wellbeing), health alerts, a message center for communicating with physicians/care teams, etc.

The mobile health application can include functionality to synchronize data captured from multiple EHRs 768 and other mobile applications with the healthcare server 766. This synchronization allows for cloud storage of the patient's aggregate health information, including the patch data. All the user's health data centrally stored in the user's EHR 768 can then be processed and analyzed on a continual basis by the healthcare server's AI engine.

Figure 8:
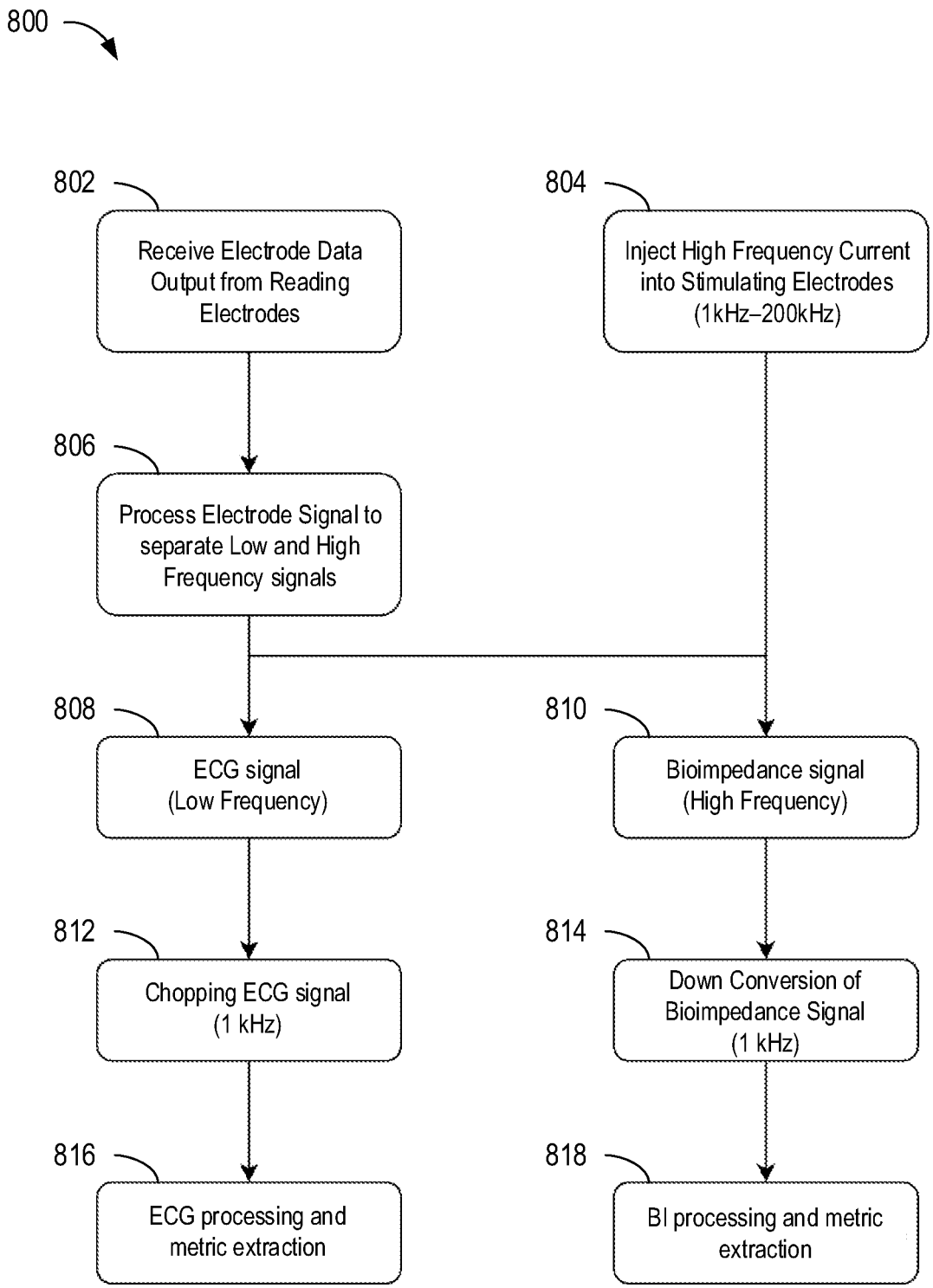
FIG. 8 is a flowchart depicting a process for performing measurements using an ECG/BI measurement system, according to certain aspects of the present disclosure.

FIG. 8 is a flowchart depicting a process 800 for performing measurements using an ECG/BI measurement system, according to certain aspects of the present disclosure. Process 800 can be performed by any suitable ECG/BI measurement system, such as ECG/BI measurement system 102 of the smart patch 100 of FIG. 1.

At block 802, electrode data output can be received from a pair of electrodes (e.g., reading electrodes). The electrode data output can be a sensed signal sensed over a pair of electrodes (e.g., inner electrodes). In some cases, simultaneous with receiving electrode data output at block 802, an injection current can be provided at block 804.

At block 804, an injection current can be provided via a pair of electrodes (e.g., stimulating electrodes). In some cases, the injection current can be a high-frequency current. In some cases, the injection current is a single-frequency current (e.g., at a frequency between 1 kHz and 200 kHz). In some cases, the injection current includes a sweeping current (e.g., a current that changes frequency over time, such as changing frequency between a first endpoint and a second endpoint within the range of 1 kHz and 200 kHz). In some cases, the injection current includes multiple components of different frequencies (e.g., a current having multiple components that each have different frequencies within the range of 1 kHz and 200 kHz).

The stimulating current can be injected at a frequency of 50 kHz, or any other suitable frequency in the range of 10 kHz-200 kHz or 1 kHz-200 kHz. In some cases, such as when the BI measurements are being used for bioimpedance spectroscopy (BIS), multiple frequencies can be generated. For example, multiple frequencies can be sequentially generated to measure impedance across a spectrum. In such cases, the range of frequencies can be 10 kHz-200 kHz or 1 kHz to 200 kHz.

In some cases, impedance measurements can make use of a wideband stimulation signal, such as a square wave, chirp, maximum length sequence (MLS) or sinusoidal wave. A square wave usually suffers from lower magnitudes at higher frequencies and a chirp waveform often leads to a low signal-to-noise ratio. Consequently, a sinusoidal wave or a MLS may be preferably applied as the injection current (e.g., stimulating current) for BI measurements. In some cases, the selected waveform maintains an equally distributed or approximately equally distributed power spectrum, as well as a low noise ratio, throughout its frequency range. As such, either a sinusoidal signal or an MLS can be useful in acquiring BI measurements with low power consumption.

In certain aspects of the present disclosure, two pairs of electrodes are provided in a nested, linear array. In such an array, the inner electrodes may be shared between measuring impedance voltage and measuring ECG signals (e.g., acting as RA and LA electrodes). In some cases, one of the electrodes is connected (e.g., permanently or switchable) to both the V+ input of the BI circuitry and the RA input of the ECG circuitry, while the other of the electrodes is connected (e.g., permanently or switchable) to the V− input of the BI circuitry and the LA input of the ECG circuitry. This configuration can be especially useful when performing BI measurements and ECG lead I measurements simultaneously.

In some cases, process 800 enables parallel analysis of real-time ECG signals and BI data acquisition. Once the stimulating electrodes inject current at block 804, the reading electrodes can receive the electrode signal at block 802. This electrode signal can include components associated with ECG measurements and components associated with BI measurements. These components are found to be present in different frequency bands within the electrode signal.

At block 806, the electrode signal can be processed to separate an ECG signal and a BI signal from the electrode signal. Separation of the ECG signal and BI signal can occur via filtering of the electrode signal. From the electrode signal, the low-frequency baseband signal can correspond to the ECG signal, and the high-frequency signal sharing frequency with the injection current can correspond to the BI signal.

To extract the ECG components, high-frequencies can be filtered out of the electrode signal (e.g., via a low-pass filter). In some cases, the electrode signal can be processed to remove frequencies above a threshold frequency. This threshold frequency can be at or approximately 150 Hz, at or approximately 100 Hz, or within a range between at or approximately 100 Hz and at or approximately 150 Hz.

The extracted ECG signal can be provided at block 808 to ECG circuitry for further processing. In some cases, further processing can include chopping the ECG signal at block 812. At block 816, the ECG signal can be additionally processed to extract physiological metrics. In some cases, the ECG can be rectified and a low-pass filter can be applied to reduce noise. In some cases, a filter can be applied to select relevant physiological metrics, such as cardiac data and/or respiratory data.

The ECG signal includes cardiorespiratory interactions that allow both cardiac and respiratory data to be obtained. The derived respiration signal is defined by certain morphological properties of the ECG particularly influenced by respiration. Therefore, the cardiac signal and parameters can be obtained by applying a high-pass filter to filter out components on the order of a user's respiration (e.g., in the approximate band of 0.05-0.5 Hz). Likewise, respiratory data can be obtained by applying a low-pass filter to filter out components not within that frequency range associated with the user's respiration. Various metrics can be extracted from the cardiac data or respiratory data. For example, cardiac data can be used to determine heart rate, heart rate variability, R-wave peak and other ECG features, and the like, and respiration data can be used to determine respiratory rate, respiration depth and other respiration features.

To extract the BI components, low-frequencies can be filtered out of the electrode signal (e.g., via a high-pass filter). In some cases, a band-pass filter can be applied to specifically filter out all but a particular band of frequencies. The cutoff frequencies used can be based on the frequency used for the injected current at block 804. For example, if the injection current is provided at a steady frequency of 50 Hz, the BI signal can be extracted by applying, to the electrode signal, a band-pass filter that passes frequencies of at or approximately 50 Hz. In another example, if the injection current is provided at a sweeping frequency between 10 kHz and 200 kHz, the BI signal can be extracted by applying, to the electrode signal, a dynamic band-pass filter that dynamically adjusts to match the sweeping frequency of the injection current (e.g., when the injection current is at 84 Hz, the dynamic band-pass filter passes 84 Hz signals). In another example, if the injection current includes multiple components at different frequencies, the BI signal can be extracted by applying, to the electrode signal, one or more band-pass filters that pass the various different frequencies of the components of the injection current.

At block 810, the BI signal can be provided to BI circuitry for additional processing. In some cases, additional processing can include down-converting the BI signal at block 814. Because of the relatively high frequencies used in the injection current, the down-conversion of the BI signal can reduce power consumption without losing important data.

At block 818, the BI signal can undergo additional processing and metric extraction. In some cases, additional processing can include demodulation of the BI signal to DC and then modulating of the signal back to baseband. In some cases, various impedance-based physiological metrics can be extracted from a BI signal, such as hydration levels, stroke volume (SV) estimation, and the like.

While described with various blocks herein, in some cases, process 800 can include additional or fewer blocks, and blocks in any suitable order.

Figure 9:
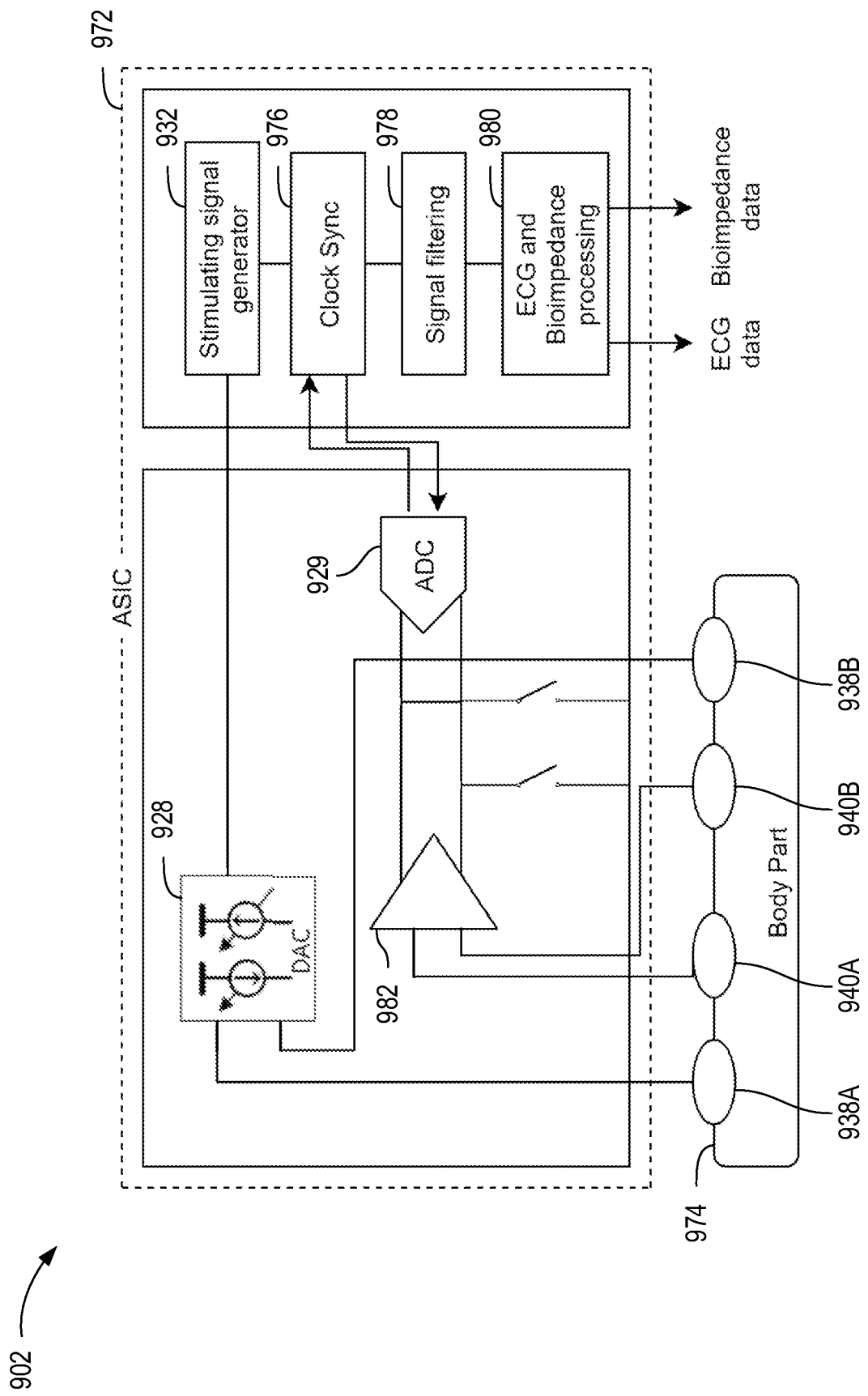
FIG. 9 is a schematic diagram depicting an ASIC of an ECG/BI measurement system, according to certain aspects of the present disclosure.

FIG. 9 is a schematic diagram depicting an ASIC 972 of an ECG/BI measurement system 902, according to certain aspects of the present disclosure. ECG/BI measurement system 902 can be any suitable ECG/BI measurement system, such as ECG/BI measurement system 102 of the smart patch 100 of FIG. 1. An ASIC 972 is used to implement certain aspects and features of the present disclosure.

ASIC 972 can provide a stimulating signal (e.g., an injection current) to a body part 974 via outer electrodes 938A, 938B. This stimulating signal can be provided by a stimulating signal generator 932 that provides a signal to a DAC 928 to drive the outer electrodes 938A, 938B at the desired frequency or frequencies.

While and/or right after the stimulating signal is being sent, a sensed signal can be received by the ASIC 972 from the inner electrodes 940A, 940B. The sensed signal can be passed through an amplifier 982 (e.g., a wideband amplifier) and to a high-speed high-resolution ADC 929. In some cases, the amplifier 982 can be a low-noise instrumentation amplifier. In some cases, the amplifier 982 can be a transconductance amplifier that converts the input voltage into current. In some cases, the ADC 929 can oversample to avoid aliasing. The output from the ADC 929 can be processed by a signal filtering module 978 and further processed by an ECG and BI processing module 980.

The ECG and BI processing module 980 can extract ECG data and BI data from a received signal, thus outputting ECG data and BI data. In some cases, the ECG and BI processing module 980 can perform a Fast Fourier Transform (FFT) on signals (e.g., an incoming signal or outgoing ECG and/or BI data signals). Additionally, in some cases, analysis of the time-variance of the BI measurements can be used to acquire a respiration signal.

In some cases, the measured signal spectrum can be normalized to data obtained from the reference resistor measurements. In this way, gain, phase, and frequency dependencies of the entire system can be compensated, and a higher measurement accuracy and bandwidth can be obtained.

A clock sync module 976 can provide a clock signal to the various components of the ASIC 972, as needed. The clock sync module 976 can synchronize with or obtain a clock signal from the main PCB of the ECG/BI measurement system 902. The clock signal can be used to facilitate deriving BI measurements from correlation with a reference signal after being filtered. The clock signal can also assist with synchronizing measurements.

Figure 10:
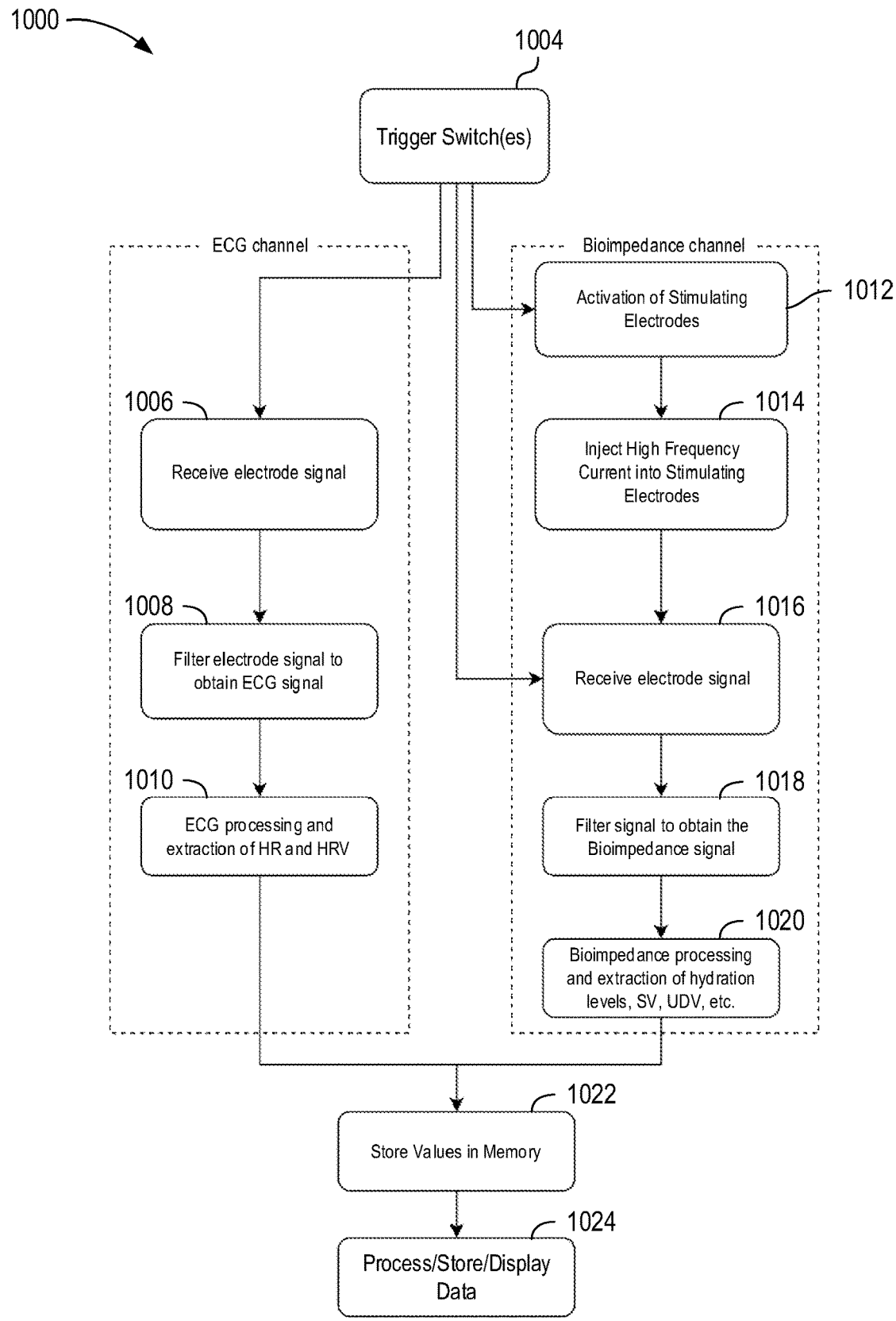
FIG. 10 is a flowchart depicting a process for performing sequential ECG and BI measurements using an ECG/BI measurement system, according to certain aspects of the present disclosure.

FIG. 10 is a flowchart depicting a process 1000 for performing sequential ECG and BI measurements using an ECG/BI measurement system, according to certain aspects of the present disclosure. Process 1000 can be performed by any suitable ECG/BI measurement system, such as ECG/BI measurement system 102 of the smart patch 100 of FIG. 1. An alternative to the filter-based, simultaneous ECG and BI monitoring consists of a switch-based sequential system (e.g., an alternating system) between ECG and BI measurement.

At block 1004, one or more switches can be triggered. In some cases, a switch can be manually triggered, such as if a user desires to specifically monitor ECG signals or BI signals, only. In some cases, however, a switch can be a controllable switch (e.g., a programmable switch). A controllable switch can be automatically triggered by a triggering event. The triggering event can be reception of a signal, such as a signal to switch monitoring modes. In some cases, however, the triggering event is a clock signal. Thus, when a clock signal is used to trigger one or more controllable switches, the switch(es) can alternate between acquiring ECG signals and acquiring BI signals at a desired frequency. The desired frequency can be any suitable frequency, such as on the order of partial-seconds, second, minute, hour, or otherwise. In an example, the desired frequency is 0.01 Hz. Thus, the switch(es) can operate to connect one or more pairs of electrodes to either ECG circuitry or BI circuitry.

When the switch is actuated to acquire ECG signals, process 1000 can continue at block 1006 by receiving an electrode signal from at least one pair of electrodes. At block 1008, the received electrode signal can be filtered as desired, and can be further processed at block 1010, such as to extract ECG-based physiological metrics. Further processing at block 1010 can be similar to processing at block 816 of FIG. 8.

When the switch is activated to acquire BI signals, process 1000 can continue from block 1004 to block 1012 and 1016. At block 1012, stimulating electrodes can be activated to provide an injection current into the skin of the user at block 1014. At block 1016, which can occur simultaneously or approximately simultaneously with block 1012, an electrode signal can be received from at least one pair of electrodes (e.g., the sensing electrodes). At block 1018, the received electrode signal can be filtered as desired, and can be further processed at block 1020, such as to extract BI-based physiological metrics. Further processing at block 1020 can be similar to processing at block 818 of FIG. 8.

The processed ECG signals and/or BI signals can be stored in a memory at block 1022, such as a memory of a wearable device or a computing device (e.g., user device, such as a smartphone or smartwatch) communicatively coupled to the ECG/BI measurement system. At block 1024, the data from the processed ECG signals and/or BI signals can be further processed, stored, displayed, or otherwise used. For example, in some cases, block 1024 can include presenting current and/or historical physiological metrics and/or other health information via a user device (e.g., a smartphone).

In some cases, a switch used at block 1004 can be an electronic switch that comprises a precision, analog switch with low power consumption, low leakage currents, and fast switching speeds. In some cases, a processor can be connected to the switch(es) and the BI and ECG circuitry to control the measurement of the ECG and BI signals. In some cases, the PCB's processor controls the measurements such that the measurements from BI circuitry and ECG circuitry are time division multiplexed.

Figure 11:
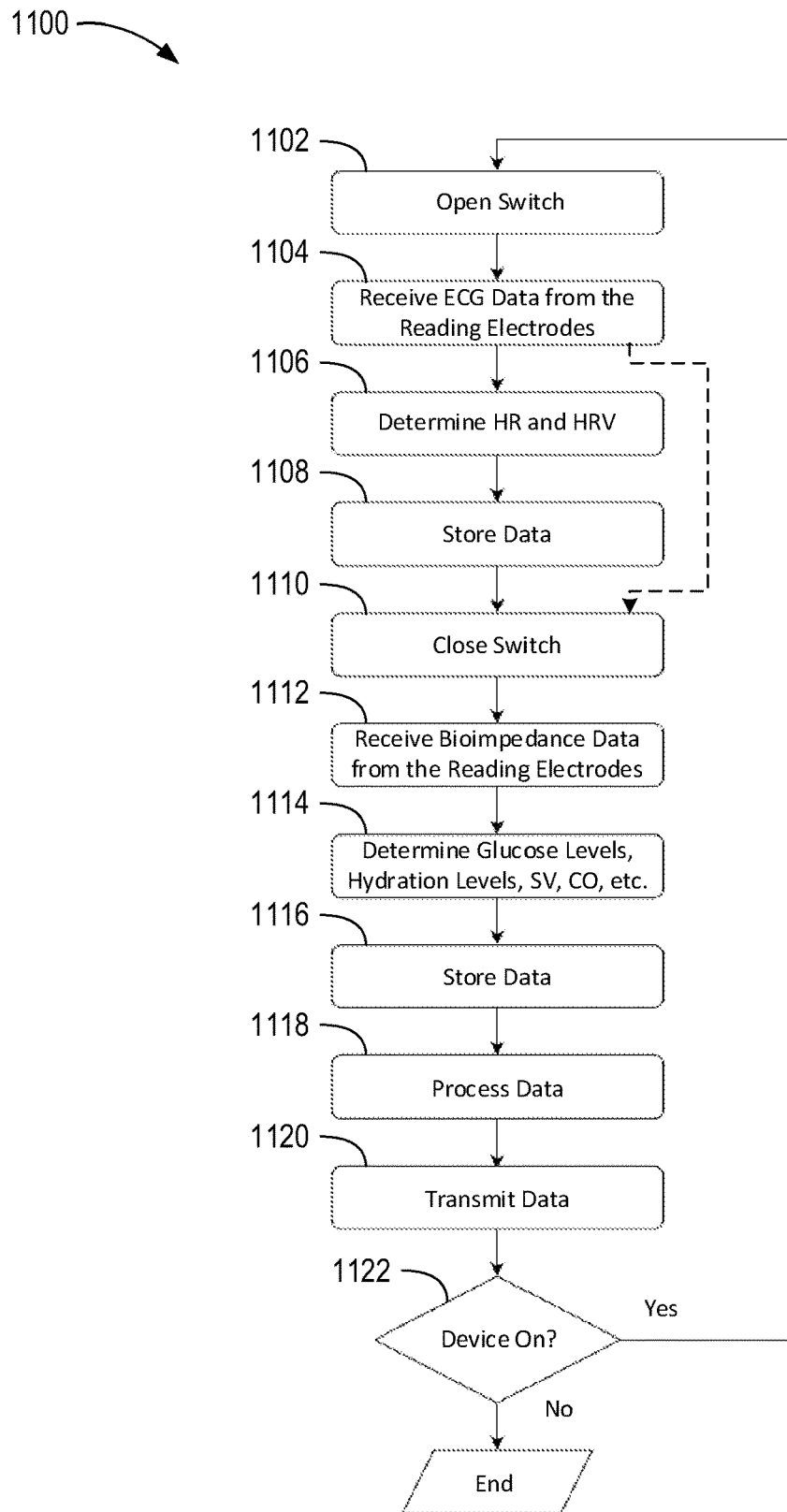
FIG. 11 is a flowchart depicting a process for performing simultaneous ECG and BI measurements using an ECG/BI measurement system, according to certain aspects of the present disclosure.

FIG. 11 is a flowchart depicting a process 1100 for performing simultaneous ECG and BI measurements using an ECG/BI measurement system, according to certain aspects of the present disclosure. Process 1100 can be performed by any suitable ECG/BI measurement system, such as ECG/BI measurement system 102 of the smart patch 100 of FIG. 1.

At block 1102, a controllable switch can be opened to electrically couple at least a first pair of electrodes (e.g., reading electrodes) to an ECG circuit of the ECG/BI measurement system. At block 1104, signals from the first pair of electrodes (and any other pairs of electrodes if multiple electrodes are used) can be received and initially processed by the ECG circuit. As no injection current is being supplied by other electrodes and the electrodes in use are connected to the ECG circuitry, ECG signals can be measured.

At block 1106, heart rate and heart rate variability can be determined from the processed ECG data. Other physiological metrics can be determined instead of or in addition to heart rate and heart rate variability. At block 1108, the determined physiological metrics and/or the ECG data can be stored.

At block 1110, the controllable switch can be closed to decouple the first pair of electrodes from the ECG circuit and instead electrically couple the first pair of electrodes to the BI circuit. When controlled by a clock signal, block 1110 can occur after a set amount of time has elapsed since the switch was opened at block 1102. In some cases, closing the switch at block 1110 also causes a second pair of electrodes to be decoupled from an ECG circuit and/or be coupled to a source of an injection current. In some cases, block 1110 occurs after block 1108, however that need not always be the case. In some cases, block 1110 can occur after ECG data is received at block 1104, thus permitting the system to acquire BI signals while the ECG signals are being processed.

At block 1112, signals from the first pair of electrodes can be received and initially processed by the BI circuit. Receiving the signals at block 1112 can include supplying an injection current via a second pair of electrodes.

At block 1114, glucose levels, hydration levels, stroke volume, cardiac output, and the like can be determined from the processed BI data. Other physiological metrics can be determined instead of or in addition to those listed above. At block 1116, the determined physiological metrics and/or the BI data can be stored.

At optional block 1118, the ECG data and/or BI data can be further processed, such as to be compressed. At optional block 1120, the processed data can be transmitted, such as to a user device and/or to a healthcare server over a communication network.

At block 1122, a check can be made to determine whether or not the ECG/BI measurement system has been turned off or otherwise disabled. If it has, then process 1100 ends. If not, the process 1100 can continue with another iteration of block 1102. When the switch is controlled by a clock signal, the subsequent iteration of block 1102 can occur after a set amount of time has elapsed since the switch was closed at block 1110.

Figure 12:
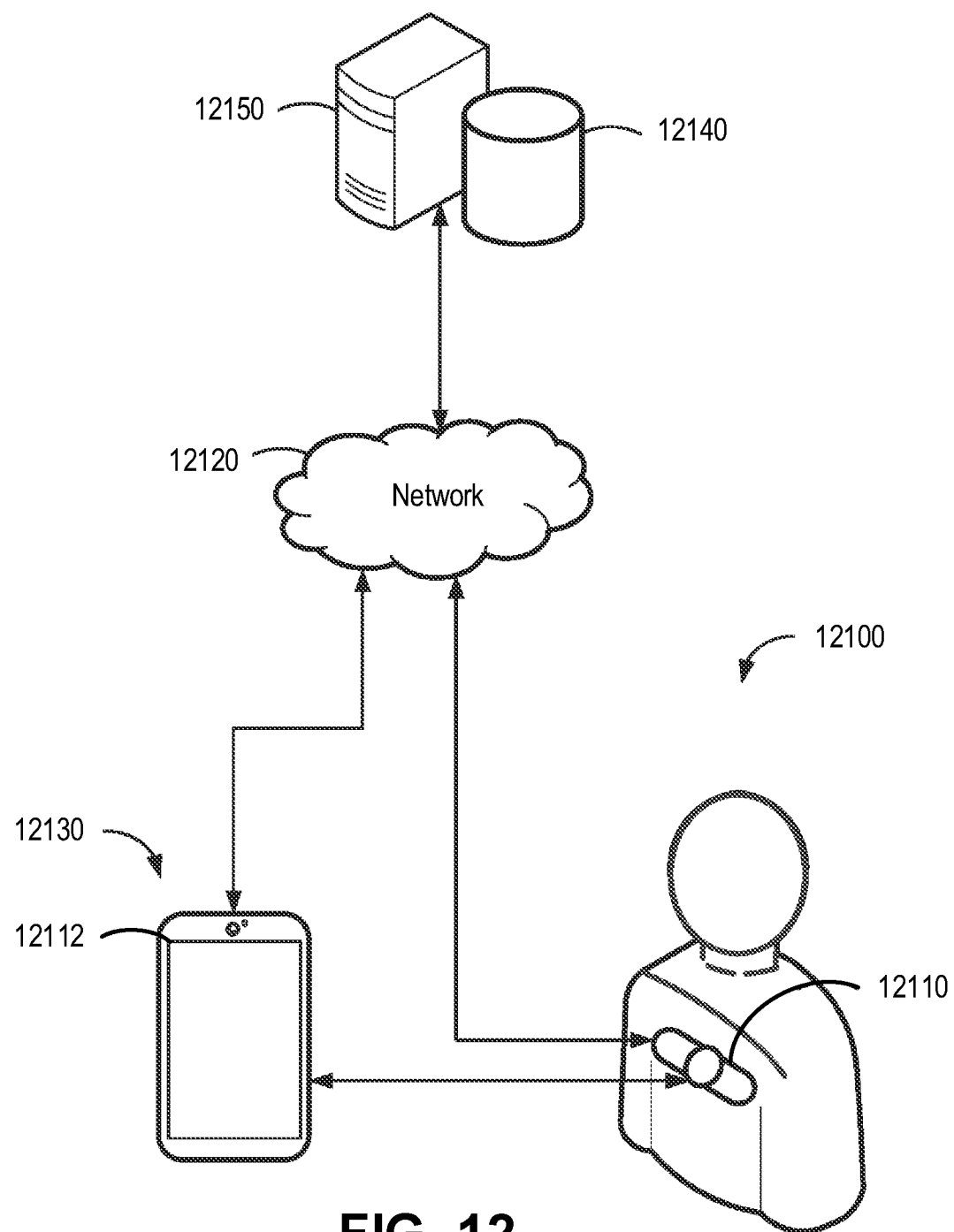
FIG. 12 illustrates an example system for implementing the disclosed technology.

FIG. 12 illustrates an example system for implementing the disclosed technology. For instance, the system may contain a computing device 12130 with a display 12112, a network 12120, a patient 12100, a wearable device 12110, a server 12150 and database 12140. The computing device 12130 may be any suitable computing device, including a computer, laptop, mobile phone, smartwatch, tablet, and the like. The network 12120 may be wired, wireless, or various combinations of wired and wireless. The network 12120 can be any suitable network, such as a personal area network, a local area network, a wide area network, a mobile network, a cloud, or the Internet. The server 12150 and database 12140 may be local, remote, and may be combinations of servers 12150 and databases 12140, or could be local processors and memory.

The wearable device 12110 may be a smartwatch, smart ankle bracelet, smart glasses, smart ring, smart patch, band, smart bra, smart clothing, digital stethoscope, or other device that suitably could be retained on the user 12100 and give access to the patient's 12100 skin to various sensors on the wearable device 12110. In some examples, the wearable device 12110 may include adhesive and stick onto a patient's 12100 skin on the neck, chest, arm, leg, torso, back or other suitable locations.

Figure 13:
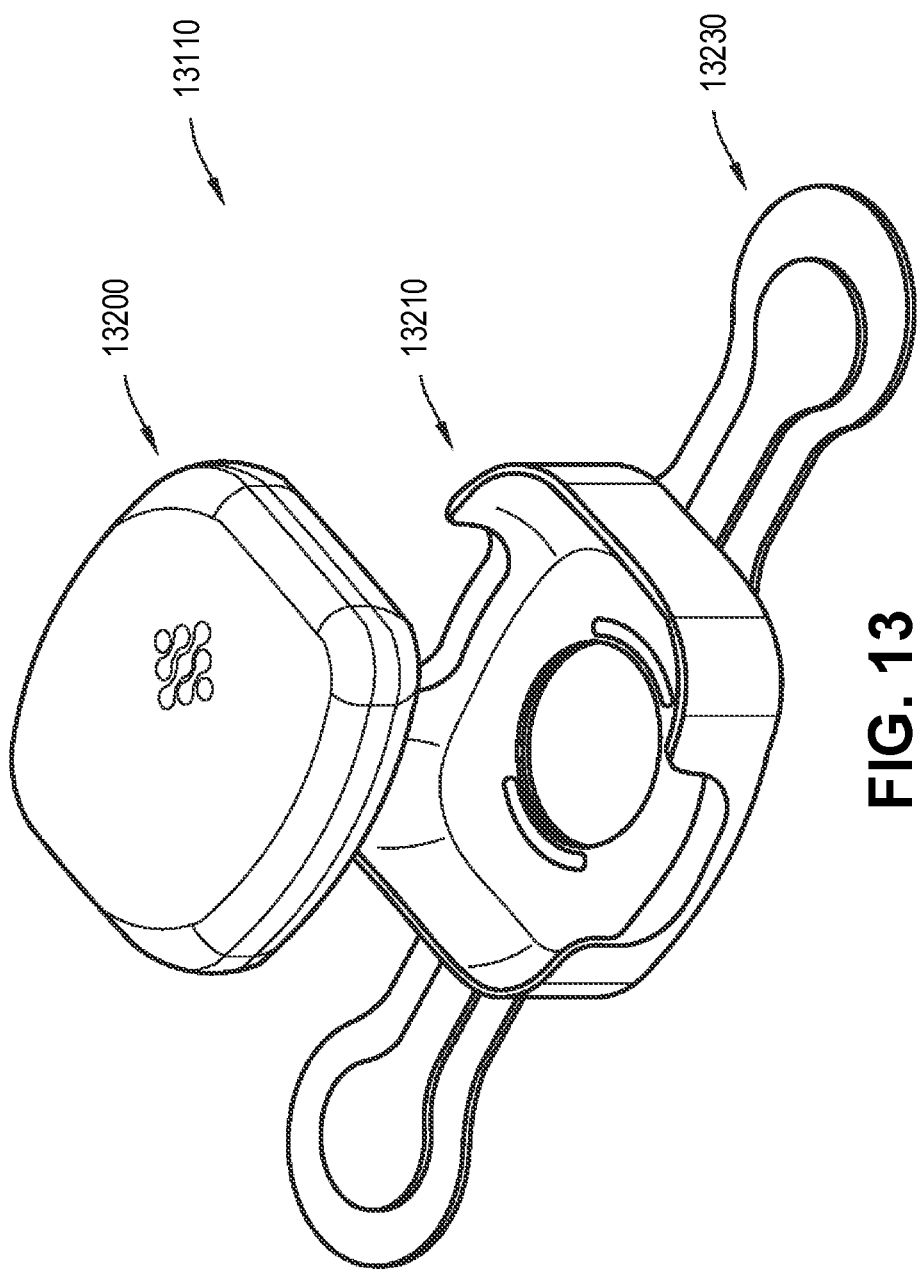
FIG. 13 is a partially exploded graphical projection of a patch for non-invasive health monitoring, according to certain aspects of the present disclosure.

FIG. 13 provides an example overview of a wearable device 13110 according to certain aspects of the present disclosure. The wearable device 13110 can be any suitable wearable device, such as wearable device 12110 of FIG. 12. The wearable device 13110 may include a sensor module 13200 (e.g., an electronics module, similar to electronics module 106 of FIG. 1), a cradle 13210, and electrodes 13230. In some examples, the electrodes 13230 may only include two, three, four, five, or six electrodes. In other examples, it may include more electrodes. In other examples, the wearable device 13110 may only include a sensor module 13200 and electrodes 13230. In still other examples, the wearable device 13110 may only be electrodes 13230 connected to a clinical grade ECG machine. The sensor module 13200 may incorporate a wireless transmitter (e.g. Bluetooth, WiFi, mobile network, and the like), various circuit boards, memory, processors and other electrical components and also may include a wired connection to a signal processor. The sensor module 13200 may also include electrical contacts that connect to the electrodes.

The sensor module 13200 may also include a PPG sensor that includes LEDs and photodiodes or other optical sensors. Accordingly, the PPG sensor may be utilized to detect the heart rate or blood oxygenation. In some examples, the output of the PPG sensor may be processed to output various peak points of the heart cycle, that include the systolic peak point, diastolic peak point, and the maximum peak point of the venus pulse that correlates to the cardiac cycle. These peak points can be utilized to determine the heart rate based on the time intervals between specific peak points.

The cradle 13210 may allow the sensor module 13200 to be removably attached from the cradle 13210 so that the sensor module 13200 could be recharged or cleaned without removing the electrodes 13230 from the patient. The cradle 13210 may attach to the sensor module 13200 using a pressure fit, snap, latch, or other suitable methods. In some examples the cradle 13210 has a window or opening that allows the PPG sensor on the sensor module 13200 to optically detect the heart rate and blood oxygenation.

The electrodes 13230 may be any suitable electrodes for detecting electrical signals from a patient's skin, and performing an ECG analysis and/or bioimpedance analysis (e.g., using bioimpedance spectroscopy). For instance, the electrodes may be adhesive electrodes that attach to the patient's skin. In some examples, this may only include two electrodes. In other examples, there may be three, four, five, six or more electrodes. The electrodes 13230 may also be any suitable electrodes for use with a clinical grade ECG system. In some cases, the electrodes 13230 may include two electrodes that are equivalent to or representative of standard electrodes (e.g., electrode placements) of a conventional ECG, such as the left arm (LA) and right arm (RA) electrodes. In other examples, the system could include up to ten electrodes, or other suitable electrode configurations, for example, as described in U.S. Pat. No. 8,200,320 issued to Kovacs, and U.S. Patent Publication No. 2019/0117100 issued to Rollie et al., and U.S. Pat. No. 10,299,691 issued to Hughes, the content of all of which are incorporated by reference in their entirety.

In some cases, additional external electrodes can be used in conjunction with the electrodes 13230. In such cases, one or more additional external electrodes can couple to the sensor module 13200 via a cable or other flexible connector that couples to the sensor module 13200 via an electrical connector (e.g., a plug, a pin, or any other suitable connector). Thus, while the wearable device 13110 may be attached to a user at a first location, one or more additional external electrodes can be simultaneously attached to the user at other locations spaced apart from the first location. These additional external electrodes can facilitate the acquisition of additional ECG data. For example, with the wearable device 13110 positioned on the user's chest adjacent the heart, additional external electrodes placed on the user's right and left legs and coupled to the sensor module 13200 can facilitate acquisition of ECG measurements that would normally involve a right leg (RL) electrode and/or a left leg (LL) electrode.

Figure 14:
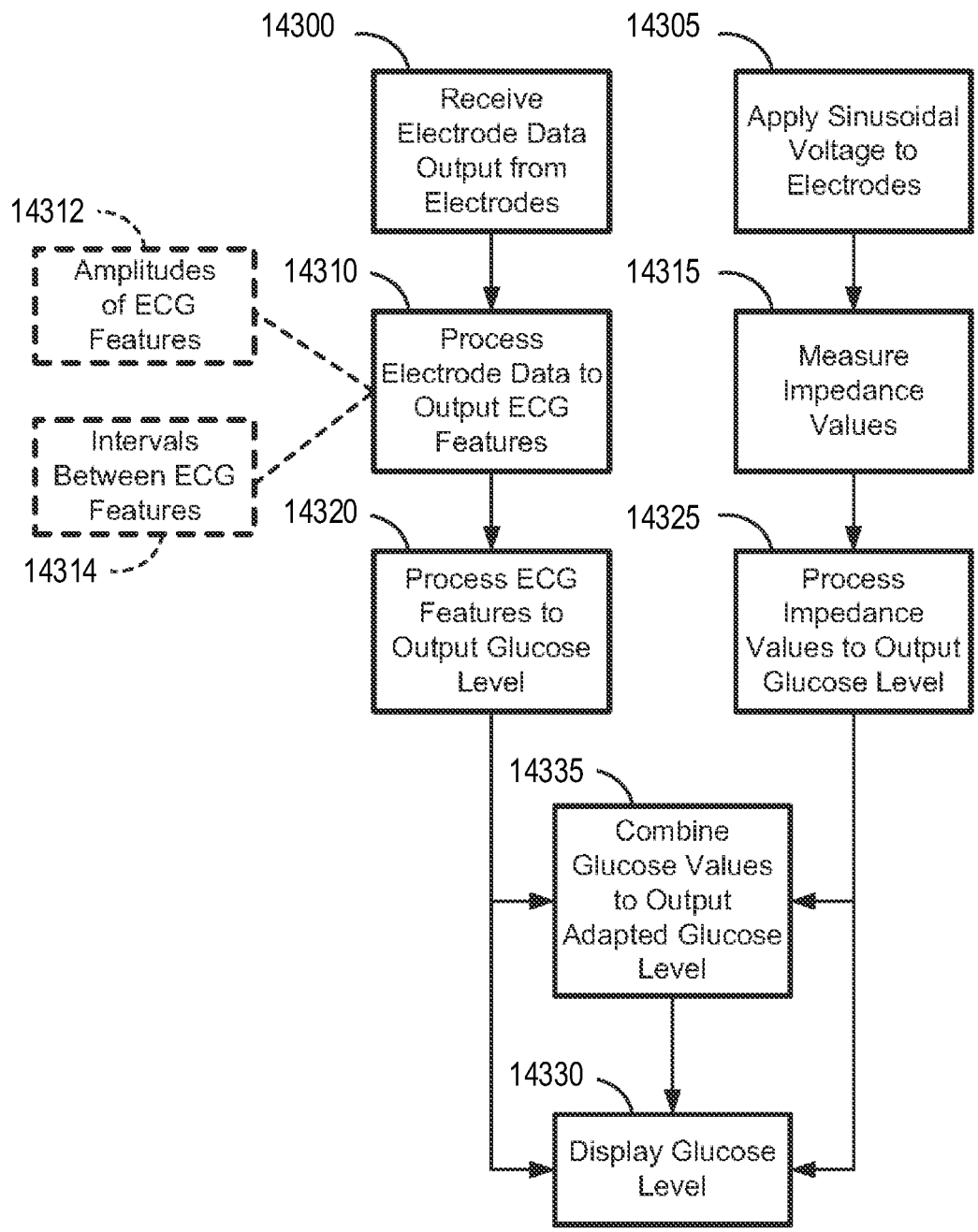
FIG. 14 is a flowchart depicting a process for measuring blood glucose, according to certain aspects of the present disclosure.

FIG. 14 is a flowchart depicting a process for obtaining a glucose level using ECG and bioimpedance measurements from a wearable device, according to certain aspects of the present disclosure. The wearable device can be any suitable wearable device, such as wearable device 12110 of FIG. 12 or smart patch 100 of FIG. 1.

As illustrated in FIG. 14, the system may determine the ECG-based blood glucose level by first receiving electrode data output from the electrodes 14300 that represents electrical activity of the heart sensed on the patient's 12100 skin. Then, the system may process the electrode data to output ECG features 14310.

To process the electrode data into ECG features, the signal may be amplified and filtered (e.g. low-pass filters, notch filters, high-pass filters). For instance, in some examples, a commercially available front-end ECG signal conditioner may be utilized, including the AD8232. In this example, front-end signal conditioning systems like the AD8232 are designed to extract, amplify and filter small bio-potential signals in the presence of noisy conditions, such as those created by motion of the patient (e.g., patient 12100 of FIG. 12) or remote electrode placement. This is particularly advantageous, as the wearable device signals from the electrodes may be relatively noisy when the patient or user is moving around as the wearable device is designed to continuously or periodically determine blood glucose levels at different times of day. Furthermore, front-end systems like the AD8232 are additionally advantageous because they can determine whether both of the electrodes of an electrode pair are in contact with the skin and can save power by not initiating processing of the ECG signal unless both electrodes of an electrode pair are in contact.

The ECG features that may be output 14310 include a variety of different time periods, amplitudes and other features. For instance, the features may include amplitude differences 14312 between certain landmarks or points on the ECG signal, or time periods/intervals 14314 between certain points on the ECG signal. Examples of features include but are not limited to the P wave, QRS complex wave, T wave), 5 feature points (P, Q, R, S, T points), PR interval (time between the beginning of the P wave and the beginning the QRS complex), the duration of the QRS complex, the ST segment, the QT interval and other suitable ECG features.

In some examples, a QRS complex may be the least noisy signal detected and therefore the Q point may serve as a reference point or reference amplitude to calculate/calibrate the various ECG features 14310. Additionally, certain ECG waves, features, and/or points may be too noisy and may be discarded as data points, for instance if they would result in an abnormally large heart rate or would be outside of other normal thresholds.

Next, the system may then process the ECG features to output a blood glucose level 14320. This is advantageous, because it has been discovered that the blood glucose level can be determined solely from ECG features. In some instances, processing the ECG features may be performed according to equation 1.

$$\text{Glucose level} = C1*(QS \text{ amplitude}/QR \text{ amplitude} + TR \text{ amplitude}/ST \text{ amplitude}) + C2*(Q\text{-}T \text{ interval}/Q\text{-}S \text{ interval}) \quad \text{Equation 1:}$$

Disclosed herein:
QS amplitude=amplitude difference between Q and S points;
QR amplitude=amplitude difference between Q and R points;
TR amplitude=amplitude difference between T and R points;
ST amplitude=amplitude difference between S and T points;
Q–T interval=time difference between Q and S points;
Q–S interval=time difference between Q and S points; and The parameters C1 and C2 may be determined during a calibration procedure by acquiring at least two or more sets of data that includes clinical-grade clean ECG signals and invasive blood glucose readings taken at the same time from the same patient 12100. Experimentation has shown that these coefficient values vary little from person-to-person, but instead are reliant on the hardware utilized. Accordingly, in some manufacturing methods, once a specific device is tested, the testing data could be utilized to determine the C1 and C2 coefficients for a specific device. In other examples, there could be universal constants determined if the hardware manufacturing process is consistent once it is determined for one or a subset of the devices.

In an example calibration procedure, glucose levels can be measured using an invasive glucose monitor, and a medical-grade ECG waveform can be acquired to derive the parameters in Equation 1 at multiple time points. Accordingly, the values recorded at each time point may be inserted into separate equations and then the equations solved to determine the values of the constants:

$$\text{Glucose Level1} = C1*k1 + C2*p1 \quad \text{Equation 2:}$$

$$\text{Glucose Level2} = C1*k2 + C2*p2 \quad \text{Equation 3:}$$

Thus, the parameters k1, p1, and k2, p2 are determined based on the measurement and testing with gold standard equipment and the variables described above. For instance, each of the above variables could be derived with the following measurements:

$k1 = (QS$ amplitude$/QR$ amplitude$+TR$ amplitude$/ST$ amplitude)measured at the time Glucose Level 1 is measured $p1 = (Q-T$ interval$/Q-S$ interval)measured at the time Glucose Level 1 is measured $k2 = (QS$ amplitude$/QR$ amplitude$+TR$ amplitude$/ST$ amplitude)measured at the time Glucose Level2 is measured $p2 = (Q-T$ interval$/Q-S$ interval)measured at the time Glucose Level2 is measured Thus, the above two equations can be solved to identify the parameters C1 and C2. In other examples, additional measurements and equations may be utilized to refine the constants, for instance with 3, 4, 5, 8, or 10 measurements. Accordingly, the values of these constants may be stored in the memory of the device, and may be reused for additionally manufactured devices as long as there are no changes to the devices.

While this specific equation has been shown to output accurate glucose results, various other combinations of the amplitudes 14312, intervals 14314 and other ECG features may be processed with a linear or other equation to determine blood glucose levels 14320.

Next, and as described in greater detail herein, the ECG-based blood glucose levels could be combined with the bioimpedance-based blood glucose levels 14325 to output an adapted glucose level 14335 as described in greater detail below. These values could then be displayed 14330 and/or stored in a database (e.g., database 12140 of FIG. 12) or provided for other various uses.

Figure 15:
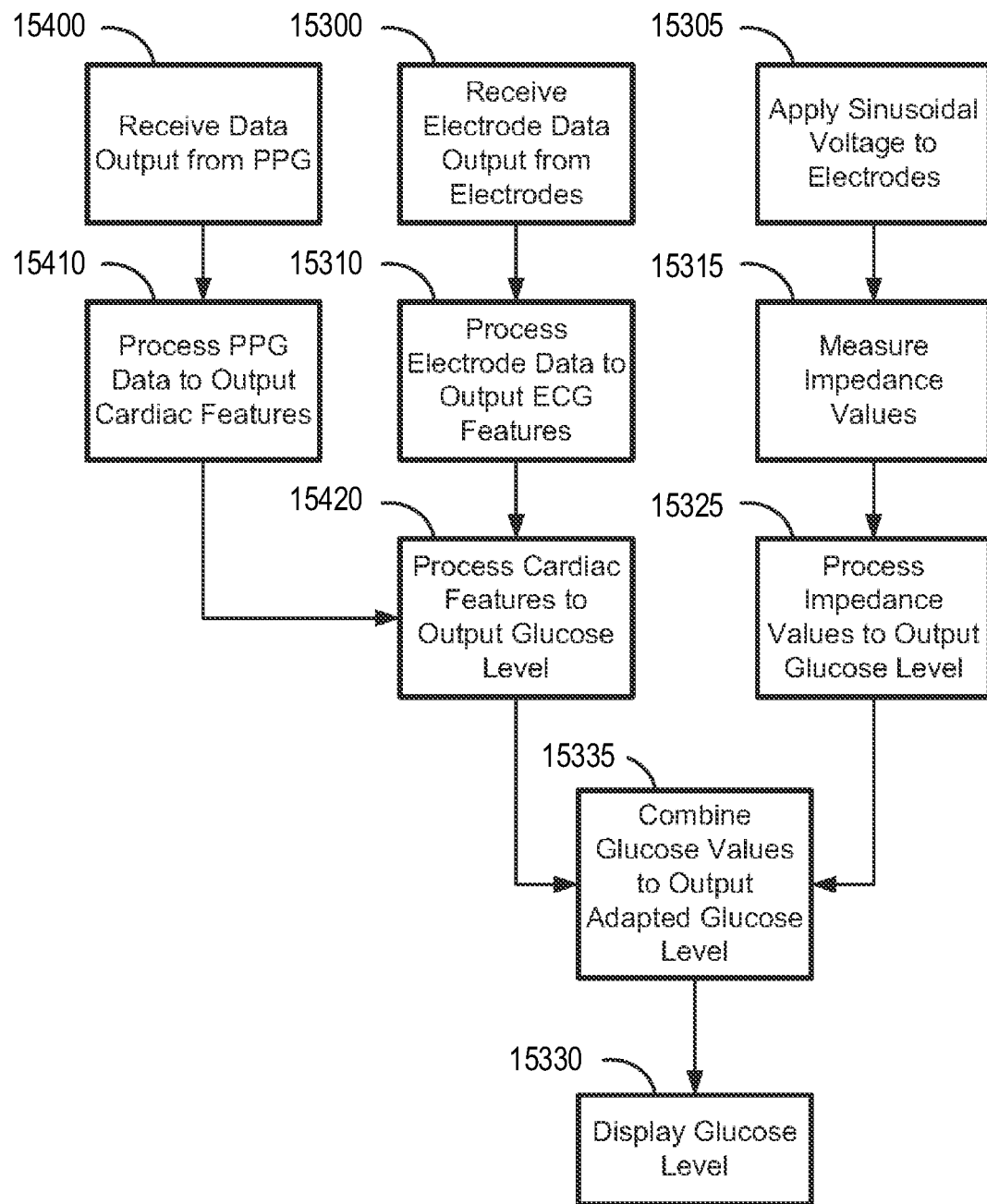
FIG. 15 is a flowchart depicting a process for measuring blood glucose, according to certain aspects of the present disclosure.

FIG. 15 is a flowchart depicting a process for obtaining a glucose level using PPG, ECG, and bioimpedance measurements from a wearable device, according to certain aspects of the present disclosure. The wearable device can be any suitable wearable device, such as wearable device 12110 of FIG. 12 or smart patch 100 of FIG. 1. The process depicted in FIG. 15 can include similar steps to the process depicted in FIG. 14.

As illustrated in FIG. 15, the system may determine the ECG-based blood glucose level by first receiving electrode data output from the electrodes 15300 that represents electrical activity of the heart sensed on the patient's skin. Then, the system may process the electrode data to output ECG features 15310.

In some examples, the ECG signal acquired from the electrodes may be too noisy to identify the ECG points and/or features with sufficient accuracy. For instance, the ECG points acquired may result in an abnormally large heart rate, or would be outside of other known physiological thresholds. Accordingly, in some examples as illustrated in FIG. 15, the PPG sensor output 15400 may be processed to identify analogous cardiac features 15410 that may be utilized to check whether the ECG acquired features are accurate, or to enhance the accuracy of the ECG acquired feature points. The system may then process the cardiac features from the PPG and the ECG features to output a blood glucose level 15420.

Additionally, many of the ECG features utilized include amplitudes of the ECG signal. However, frequently, noise may cause various amplitudes of the ECG signal to be inaccurate. However, the PPG signal has highly accurate peak amplitudes of the cardiac cycle.

Accordingly, these amplitudes may be utilized to calibrate the ECG signal amplitudes, confirm the amplitudes are accurate, reject ECG data that doesn't match within a threshold of the PPG readings, for instance, or replace the ECG amplitudes with certain PPG-based amplitude readings. For instance, the maximum PPG amplitude could be utilized to replace the amplitudes related to the QRS complex that are utilized in Equation 1. In some examples, the amplitude of the PPG reading could be correlated to clinical-grade ECG amplitudes to determine ECG amplitudes from the PPG-based amplitudes.

In some examples, the system will determine a bioimpedance-based glucose level that can be combined with the ECG-based glucose level to output an accurate and adapted glucose level 15335. An example of a bioimpedance-based blood glucose measurement is described by Talary, et al., in "Non-Invasive Impedance based Continuous Glucose Monitoring System," published by IFMBE in 2007, the content of which is incorporated by reference herein in its entirety. The bioimpedance-based glucose levels may be determined by first applying a sinusoidal voltage to the electrodes 15305 and measuring impedance values 15315. Then, impedance values may be processed to output a blood glucose level 15325.

The impedance values of the skin are related to blood glucose levels. The values are not static but will change with various frequencies of voltage applied to the skin (e.g. sinusoidal voltages). The impedance values of the skin can be measured by any suitable methods, including by using a voltage divider or a Vector Network Analyzer.

In some examples, a low amplitude voltage (e.g. <0.3V) will be applied to the electrodes and voltage divider. In other examples various other amplitudes greater than 0.3V could be applied. Additionally, in some examples, the voltage applied will be within the range of 1 kHz-200 MHz, such as 1 MHz-160 MHz or 10 MHz-200 MHz. In other examples, other frequencies could be utilized.

Specifically, the system may scan the frequencies and detect the resulting impedance in a certain range until the system identifies the lowest impedance value. For instance, the microcontroller may sweep from 10 MHz to 200 MHz frequency range by controlling DAC values from 0 to 1024. In this example, the voltage control unit (VCO) will apply a frequency sweeping through these values every 100μ seconds. In this case, the frequency separation resolution is 100 kHz, so 1900 points could be measured to obtain an impedance response value or graph that could be stored in the database (e.g., database 12140 of FIG. 12), local memory of the patch or other wearable device, or other locations. These values may be calibrated with current temperature values, amplitudes of a QRS complex of an ECG, and heart rate values with a linear equation through experimentation.

The lowest impedance value corresponds to the resonant glucose level, which can be converted to a blood glucose level.

Lastly, the bioimpedance-based glucose level and the ECG-based glucose level may be combined to output an adapted glucose level 15335 as depicted in FIG. 14 at block 14335 and FIG. 15 at block 15335. These values may be combined using various equations or methods. In one example, these methods may be combined using the following linear formula:

Glucose level=C2*impedance glucose level+ C3*ECG glucose level     Equation 4:

Accordingly, constants C2 and C3 may be determined through experimentation using invasive glucose-based levels taken simultaneously with measured values of bioimpedance-based glucose level and the ECG-based glucose level using a device as disclosed herein. Thus, for a particular patient and a particular device, the glucose level could be measured invasively at least two different times, and at each of those times, an impedance-based glucose level and an ECG-based glucose level could be measured using a device as disclosed herein. Then, the constants could be determined by solving the set of questions derived from those values. In some examples, this could be performed, with 3, 4, 5, 10 or other suitable numbers of measurements to increase the accuracy.

The disclosed systems and methods were tested on patients and compared to invasive glucose levels. For instance, in one example, a prototype device comprising a wearable patch was developed that measured and output glucose levels by determining an adapted glucose level 15335 as disclosed herein by combining the measured ECG-based glucose level and the impedance-based glucose level.

As illustrated in Table 1 below, the test values using the disclosed systems and methods were quite close to the invasive gold standard values of blood glucose measured using the Accu-Chek Performa Blood Glucose Meter and Lancing Device (model number B9BIGGTGO).

| Patient | Test Glucose (mmol/L) | Real Glucose (mmol/L) | Difference (mmol/L) | Percent Difference |
|---|---|---|---|---|
| 1 | 5.3 | 5.1 | 0.2 | 3.92% |
| 2 | 6.8 | 7 | 0.2 | 2.86% |
| 3 | 3.4 | 3.8 | 0.4 | 10.53% |
| 4 | 5.1 | 5.4 | 0.3 | 5.56% |
| 5 | 10.7 | 10.4 | 0.3 | 2.88% |
| 6 | 6.2 | 6.3 | 0.1 | 1.59% |
| 7 | 3.1 | 3.7 | 0.6 | 16.22% |
| 8 | 5.9 | 6.2 | 0.3 | 4.84% |
| 9 | 6.5 | 6.5 | 0 | 0.00% |
| 10 | 7.8 | 7.4 | 0.4 | 5.41% |
| 11 | 5.2 | 5.4 | 0.2 | 3.70% |
| 12 | 9.4 | 9.5 | 0.1 | 1.05% |
| 13 | 9.2 | 9.6 | 0.4 | 4.17% |
| 14 | 4.2 | 4.5 | 0.3 | 6.67% |
| 15 | 4.6 | 4.3 | 0.3 | 6.98% |
| 16 | 6.7 | 6.5 | 0.2 | 3.08% |
| 17 | 7 | 7.1 | 0.1 | 1.41% |
| 18 | 5.7 | 5.4 | 0.3 | 5.56% |
| 19 | 3.2 | 3.7 | 0.5 | 13.51% |
| 20 | 2.8 | 3.1 | 0.3 | 9.68% |
| 21 | 5.8 | 5.7 | 0.1 | 1.75% |
| 22 | 5.4 | 5.2 | 0.2 | 3.85% |
| 23 | 9.7 | 9.5 | 0.2 | 2.11% |
| 24 | 9.6 | 9.7 | 0.1 | 1.03% |
| 25 | 4.1 | 4.6 | 0.5 | 10.87% |
| 26 | 5.3 | 5.1 | 0.2 | 3.92% |
| 27 | 3.7 | 3.8 | 0.1 | 2.63% |
| 28 | 6.5 | 6.4 | 0.1 | 1.56% |
| 29 | 6.4 | 6.2 | 0.2 | 3.23% |
| 30 | 6.9 | 7 | 0.1 | 1.43% |
| 31 | 6.2 | 6.2 | 0 | 0.00% |
| 32 | 5.3 | 5.1 | 0.2 | 3.92% |
| 33 | 6.8 | 7 | 0.2 | 2.86% |
| 34 | 3.4 | 3.8 | 0.4 | 10.53% |
| 35 | 5.1 | 5.4 | 0.3 | 5.56% |
| 36 | 10.7 | 10.4 | 0.3 | 2.88% |
| 37 | 6.2 | 6.3 | 0.1 | 1.59% |
| 38 | 3.1 | 3.7 | 0.6 | 16.22% |
| 39 | 5.9 | 6.3 | 0.4 | 6.35% |
| 40 | 6.5 | 6.5 | 0 | 0.00% |
| 41 | 6.1 | 6.3 | 0.2 | 3.17% |
| 42 | 9.4 | 9.5 | 0.1 | 1.05% |
| 43 | 9.2 | 9.6 | 0.4 | 4.17% |
| 44 | 5.7 | 5.4 | 0.3 | 5.56% |
| 45 | 4.2 | 4.5 | 0.3 | 6.67% |
| 46 | 3.2 | 3.7 | 0.5 | 13.51% |
| 47 | 5.8 | 5.4 | 0.4 | 7.41% |
| 48 | 6.7 | 6.5 | 0.2 | 3.08% |
| 49 | 7 | 7.2 | 0.2 | 2.78% |
| 50 | 3.7 | 3.9 | 0.2 | 5.13% |
| Average for 50 Patients | 6.05 | 6.14 | | 4.89% |

Accordingly, this experimental data illustrated there was only an average of about a 5% difference between the tested glucose level using the patch-based prototype according to the methods disclosed herein and the invasive based glucose level.

Figure 16:
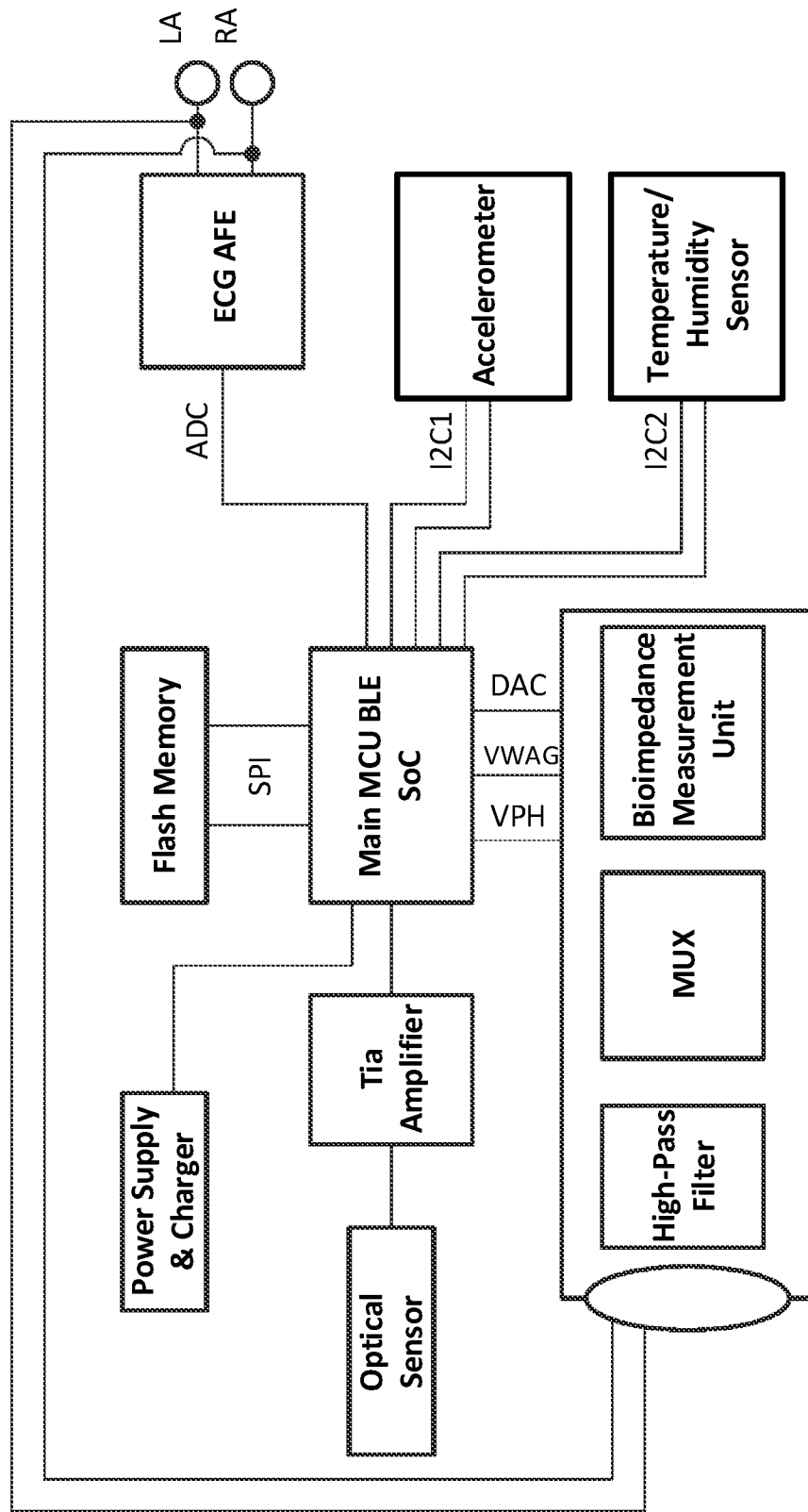
FIG. 16 is a schematic diagram showing an example system using two electrodes for performing ECG monitoring and bioimpedance measurement, according to certain aspects of the present disclosure.
Figure 17:
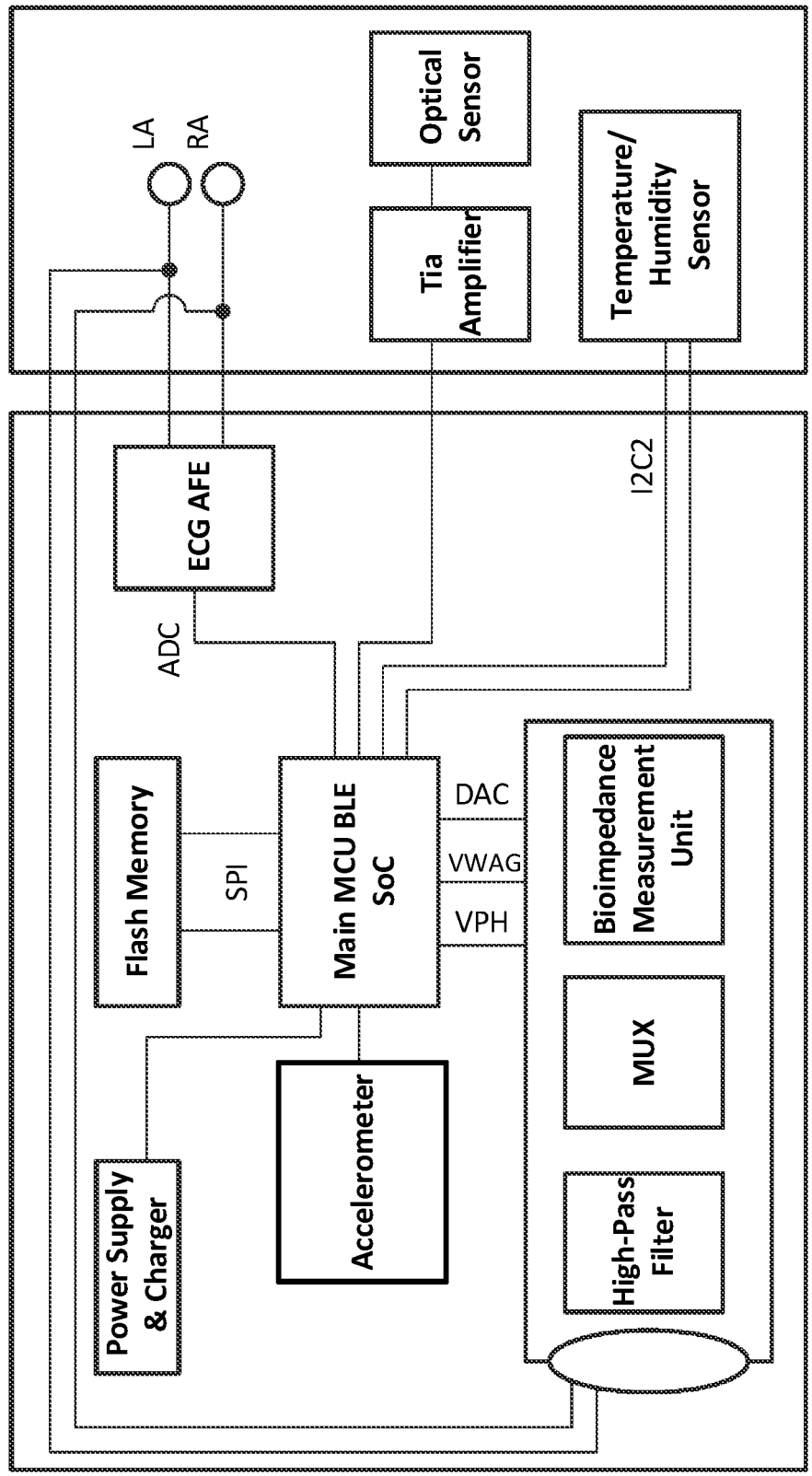
FIG. 17 is a schematic diagram showing an example system using two electrodes for performing ECG monitoring and bioimpedance measurement, according to certain aspects of the present disclosure.

FIGS. 16 and 17 illustrate example circuit diagrams of a system utilizing two electrodes connected to both an ECG front-end and a bioimpedance spectroscopy front-end. In some cases, the example circuit diagrams of FIGS. 16 and 17 may be implemented in a wearable device, such as wearable device 12110 of FIG. 12. For the impedance spectroscopy, the components may include a voltage control unit, a high-pass filter, an impedance measurement, and a multiplexer. FIG. 17 illustrates an embodiment with sensor board components separate from the main board components.

As illustrated, in some examples a single MCU is connected to the ECG front-end and the bioimpedance front-end to control both functions.

Figure 18:
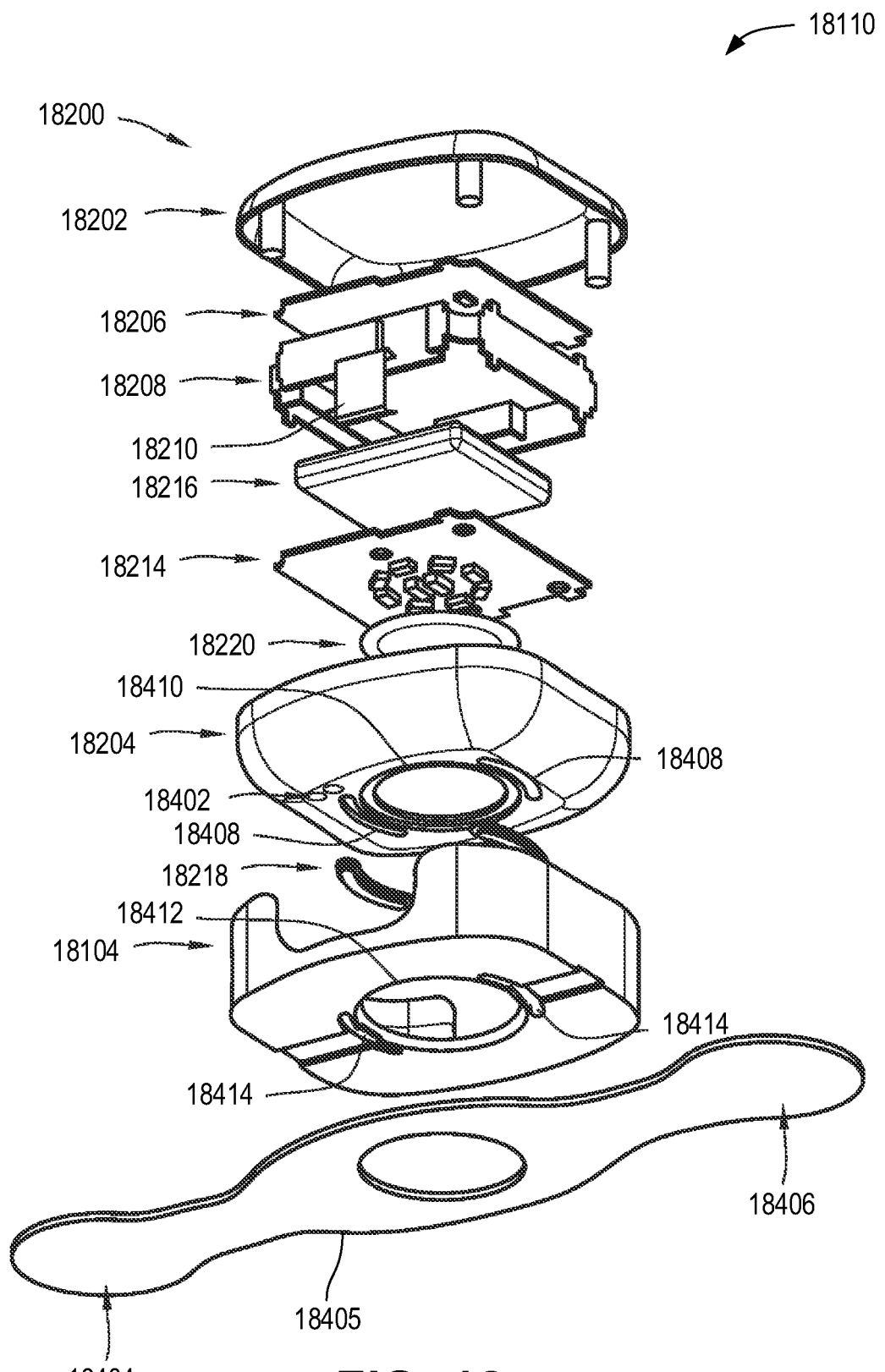
FIG. 18 is an exploded view of an underside of a patch for health monitoring with two electrodes, according to certain aspects of the present disclosure.

FIG. 18 illustrates a two electrode configuration that can be used for ECG and bioimpedance spectroscopy measurements. The wearable device 18110 of FIG. 18 can be any suitable wearable device, such as wearable device 12110 of FIG. 12. In some cases, an electrode sitting at position 18404 on an adhesive substrate 18405 can represent an LA terminal for ECG measurements, and an electrode sitting at position 18406 on the adhesive substrate 18405 can represent the RA terminal. Also in FIG. 18, one or more charging ports 18402 are provided for interfacing the body of the electronics module 18200 to a charging station.

Additionally, FIG. 18 illustrates components in the wearable device 18110, according to some implementations of the present disclosure. The electronics module 18200 of the wearable device 18110 includes the top housing portion 18202 and the bottom housing portion 18204. Enclosed within the top housing portion 18202 and the bottom housing portion 18204 are the main PCB 18206, the holder 18208, the flexible PCB connector 18210, the battery 18216, and the sensor board 18214. The bottom housing portion 18204 can include one or more housing openings, for example, the housing openings 18408, and/or one or more housing windows, for example, the housing window 18410.

The housing window material 18220 is engineered to cover the housing window 18410. The housing window material 18220 protects the electronic components of the electronics module 18200 from outside elements, for example, liquid, dust, and/or other particles. The housing window material 18220 prevents these outside elements from entering the electronics module 18200 via the housing window 18410. The housing window material 18220 can be a translucent material including plastic, sapphire crystals, mineral crystals, plexiglass, hesalite crystals, glass, etc. Although the housing window material 18220 and the housing window 18410 are shown to have a circular shape, other shapes can be used. For example, the housing window material 18220 and the housing window 18410 can be shaped as a square, a rectangle, a polygon, etc.

The housing window 18410 is provided as an example, but more than one housing window can be provided. For example, the wearable device 18110 can have as many housing windows as a total number of photodetectors and light emitters. In another example, the wearable device 18110 can have as many housing windows as a total number of line-of-sight sensors, for example optical sensors, imaging sensors, thermal imaging sensors, laser sensors, etc. Each respective photodetector and/or light emitters can have a dedicated housing window or can share a housing window with another photodetector and/or light emitter. For example, two light emitters can share a housing window, two photodetectors share another housing window, three photodetectors share yet another housing window, and one photodetector has its dedicated housing window. A housing window material can be provided for all housing windows of the bottom housing portion 18204.

The housing openings 18408, different from the housing window 18410, are configured to allow electrical connections to the sensor board 18214 from components outside the electronics module 18200. The housing openings 18408 can take the shape of one or more metal connectors 18218 that interface with the housing opening 18408. The one or more metal connectors 18218 are designed to plug the housing openings 18408 such that the housing openings 18408 are sealed when the electronics module 18200 is coupled to the base 18104.

In some implementations, the base 18104 includes a base window 18412. The base window 18412 is shown as substantially circular, but other shapes can be envisioned. Unlike the housing window 18410, the base window 18412 is not filled with any material and is just an opening that substantially matches the housing window 18410 on the electronics module 18200. When the electronics module 18200 is coupled to the base 18104, the housing window 18410 and the base window 18412 are aligned such that sensors on the sensor board 18214 can send light from the sensor board 18214 to the base window 18412 via the housing window 18410, and the sensors on the sensor board 18214 can receive light from the base window 18412 via the housing window 18410.

In some implementations, the base 18104 includes one or more electrode openings 18414 for receiving elements to connect the electrodes to the PCB 18214. The electrode openings 18414 can have a shape that substantially matches the one or more metal connectors 18218. The electrode openings 18414 can also have a shape that substantially matches a connecting element that couples the electrodes to the sensor board 18214.

In some implementations, one or more metal connectors 18218 are configured to receive electrode ends. The electrode ends can protrude from the one or more electrode openings, and the one or more metal connectors 18218 can snap onto the electrode ends. When snapped onto the electrode ends, the one or more metal connectors 18218 have an electrical connection to the electrodes. When snapped onto the electrode ends, the one or more metal connectors 18218 hold the base 18104 in place between the electrodes and the one or more metal connectors 18218.

In some implementations, the one or more metal connectors 18218 are configured to be inserted in the one or more electrode openings 18414 in the base 18104 (from the inner surface of the base 18104). When inserted, the one or more metal connectors 18218 make contact with the electrode ends inserted from the outer surface of the base 18104. The one or more metal connectors 18218 and the electrode ends are designed to fit snugly into the one or more electrode openings 18414.

In some implementations, the adhesive substrate 18405 not only supports and secures the electrodes on the user's skin, but a top layer of the adhesive substrate 18405 contacting the base 18104 can removably attach to the outer surface of the base 18104. The electronics module 18200 can be designed to plug into and out of the base 18104, allowing the base 18104 to send ECG electrical signals to the sensor board 18214. The base 18104 can be designed to allow for easy replacement of the adhesive substrate 18405 if the adhesive layer, electrodes, or other layers are broken or old.

Figure 19:
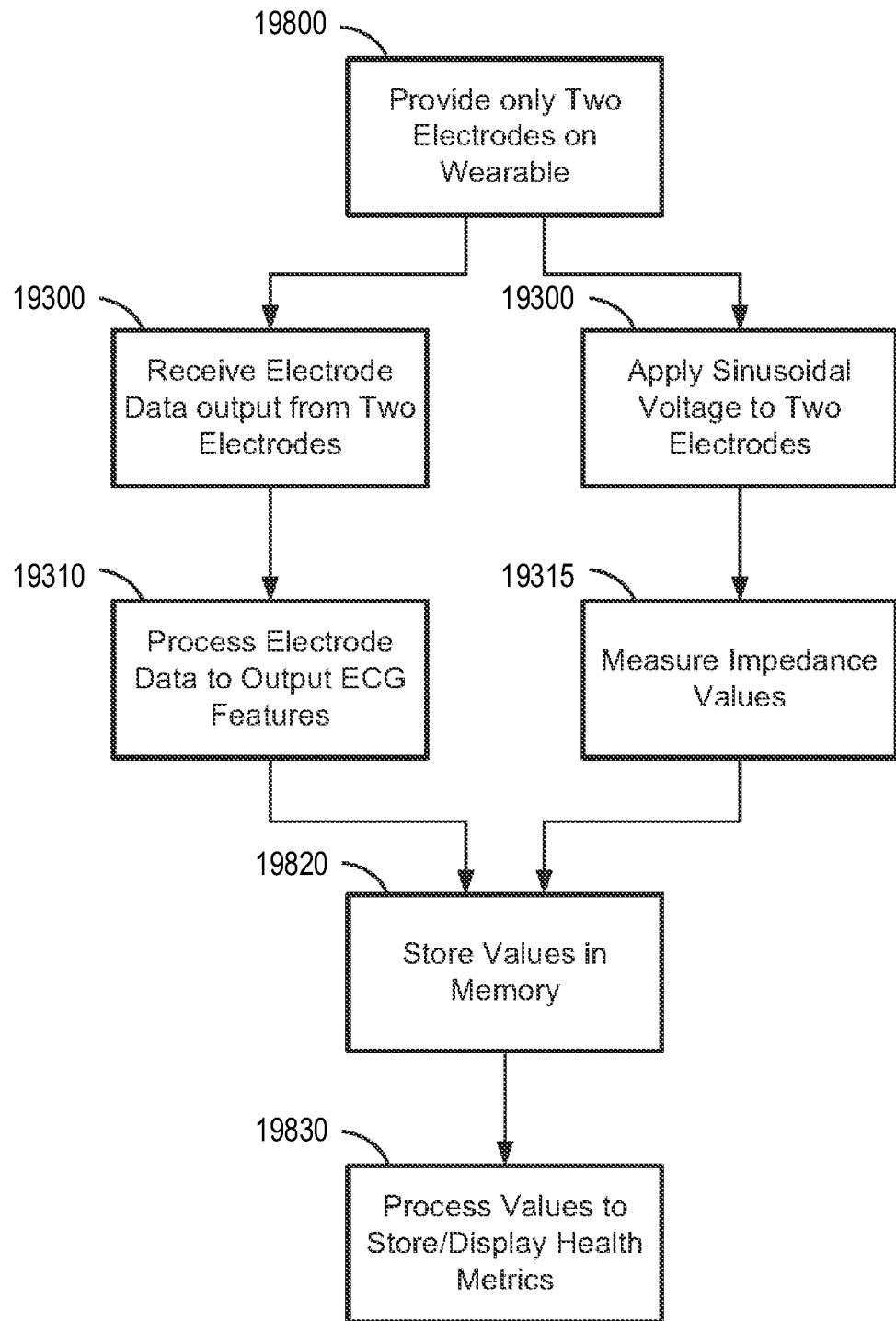
FIG. 19 is a flowchart depicting a process for sharing a pair of electrodes to monitor ECG features and perform bioimpedance measurement, according to certain aspects of the present disclosure.

FIG. 19 illustrates an example method for performing ECG and bioimpedance spectroscopy measurements using the disclosed systems. For instance, as disclosed herein various wearable devices (e.g., wearable device 12110 of FIG. 12) may be provided that have only two, three, or more electrodes at block 19800. Then, these wearable devices may be worn by the patient to periodically measure the health metrics or for other applications disclosed herein.

Accordingly, at block 19800 the system may further receive electrode data output from the two electrodes at various times, and process the electrode data to output ECG features at block 19310. In some examples, the system may use a frequency filter (e.g. low-pass filter) to filter out signals other than the ECG signals. For instance, the low-pass filter will filter out the higher frequencies applied to the electrodes for bioimpedance spectroscopy measurements. Then, the ECG features may be stored in memory at block 19820 and/or further processed to determine and store/display various health metrics at block 19830.

Additionally, the system may apply sinusoidal voltage at varying frequencies (particularly outside the ECG frequency range to avoid interference with the ECG signal) to the two or more electrodes at block 19305 and then measure the impedance values at block 19315 due to the skin-electrode impedance. For example, a square-wave current at 2 kHz and known amplitude can be used. While measuring impedance values, the system may apply a high-pass filter to remove ECG related noise and other noise not related to the applied sinusoidal voltage. In some examples, a band-pass filter could be used that changes as the sinusoidal voltage is applied. Furthermore, by demodulating the impedance signal to DC, the sampling rate of the impedance channels can be minimized, reducing power consumption.

Thus, the two electrodes may be switched between passive monitoring of ECG signals and applying voltage at different frequencies to perform impedance spectroscopy. The timing and filtering are quite important, as in some examples, both the ECG measurements and impedance spectroscopy measurements from nearly the same point in time will be utilized to determine a patient's blood glucose levels. Additionally, because the same electrodes are utilized, filtering is quite important to avoid noise and contamination of signal.

It should initially be understood that the disclosure herein may be implemented with any type of hardware and/or software, and may be a pre-programmed general purpose computing device. For example, the system may be implemented using a server, a personal computer, a portable computer, a thin client, a wearable device, a digital stethoscope, or any suitable device or devices. The disclosure and/or components thereof may be a single device at a single location, or multiple devices at a single location or multiple locations that are connected together using any appropriate communication protocols over any communication medium such as electric cable, fiber optic cable, or in a wireless manner.

It should also be noted that the disclosure is illustrated and discussed herein as having a plurality of modules which perform particular functions. It should be understood that these modules are merely schematically illustrated based on their function for clarity purposes only, and do not necessarily represent specific hardware or software. In this regard, these modules may be hardware and/or software implemented to substantially perform the particular functions discussed. Moreover, the modules may be combined together within the disclosure, or divided into additional modules based on the particular function desired. Thus, the disclosure should not be construed to limit the present invention, but merely be understood to illustrate one example implementation thereof.

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks), and any wireless networks.

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, flash memory, or other storage devices).

The operations described in this specification can be implemented as operations performed by a "data processing apparatus" on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, multi-core processors, GPUs, AI-accelerators, in-memory computing architectures or combinations, of the foregoing. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures, and deep learning and artificial intelligence computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, flash memory or optical disks. However, a computer need not have such devices. Moreover, a computer can be embedded in another device, e.g., a mobile telephone, a personal digital assistant (PDA), smartwatch, smart glasses, patch, wearable devices, a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

The foregoing description of the embodiments, including illustrated embodiments, has been presented only for the purpose of illustration and description and is not intended to be exhaustive or limiting to the precise forms disclosed. Numerous modifications, adaptations, and uses thereof will be apparent to those skilled in the art. Numerous changes to the disclosed embodiments can be made in accordance with the disclosure herein, without departing from the spirit or scope of the invention. Thus, the breadth and scope of the present invention should not be limited by any of the above-described embodiments.

While operations may be depicted in the drawings in a particular order, the depicted order should not be understood as necessarily requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Although the invention has been illustrated and described with respect to one or more implementations, equivalent alterations and modifications will occur or be known to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

As used below, any reference to a series of examples is to be understood as a reference to each of those examples disjunctively (e.g., "Examples 1-4" is to be understood as "Examples 1, 2, 3, or 4").

Example 1 is a system, comprising: a first pair of electrodes electrically couplable to skin of a user; a second pair of electrodes electrically couplable to the skin of the user, wherein the first pair of electrodes and the second pair of electrodes are arranged in a linear array; and a control system coupled to the first pair of electrodes and the second pair of electrodes, the control system configured to perform operations including: providing an injection current via the first pair of electrodes; acquiring a sensed signal via the second pair of electrodes; and determining electrocardiogram (ECG) measurements and bioimpedance (BI) measurements from the sensed signal.

Example 2 is the system of example(s) 1, wherein the second pair of electrodes are positioned within a space defined between each electrode of the first pair of electrodes.

Example 3 is the system of example(s) 1 or 2, wherein the control system is housed within an electronics module of a wearable device, and wherein the first pair of electrodes and the second pair of electrodes are each electrically coupled to the skin of the user when the wearable device is worn by the user.

Example 4 is the system of example(s) 3, wherein the wearable device is a patch, wherein the electronics module is coupled to a patch substrate, wherein the first pair of electrodes and the second pair of electrodes are embedded within the patch substrate, and wherein the patch substrate includes an adhesive layer to secure the patch to the skin of the user.

Example 5 is the system of example(s) 4, wherein the patch substrate further comprises conductive gel disposed on respective exposed surfaces of each of the electrodes of the first pair of electrodes and the second pair of electrodes.

Example 6 is the system of example(s) 3-5, wherein the electronics module is waterproof or water-resistant, and wherein the wearable device is configured to be worn by the user in a wet environment.

Example 7 is the system of example(s) 1-6, wherein determining the ECG measurements and the BI measurements from the sensed signal includes: determining an ECG signal from the sensed signal; and determining a BI signal from the sensed signal.

Example 8 is the system of example(s) 7, wherein determining the ECG signal from the sensed signal includes filtering the sensed signal to extract the ECG signal from the sensed signal, and wherein determining the BI signal from the sensed signal includes filtering the sensed signal to extract the BI signal from the sensed signal.

Example 9 is the system of example(s) 7 or 8, wherein determining the ECG measurements and the BI measurements from the sensed signal further includes: down-converting the BI signal; and processing the down-converted BI signal to extract the BI measurements.

Example 10 is the system of example(s) 9, wherein providing the injection current via the first pair of electrodes includes injecting a current at or greater than an injection frequency, and wherein down-converting the BI signal includes down-converting the BI signal to a frequency at or below the injection frequency.

Example 11 is the system of example(s) 10, wherein down-converting the BI signal includes down-converting the BI signal to a frequency at or below 1 kHz.

Example 12 is the system of example(s) 7, wherein the control system includes ECG processing circuitry, BI processing circuitry, and a controllable switch coupled to the second pair of electrodes to selectively direct the sensed signal to the ECG processing circuitry or the BI processing circuitry, wherein determining the ECG signal from the sensed signal includes actuating the controllable switch to direct the sensed signal to the ECG processing circuitry, and wherein determining the BI signal from the sensed signal includes actuating the controllable switch to direct the sensed signal to the BI processing circuitry.

Example 13 is the system of example(s) 12, wherein the control system includes an internal clock for providing a clock signal, the internal clock coupled to the controllable switch to actuate the controllable switch using the clock signal.

Example 14 is the system of example(s) 12 or 13, wherein actuation of the controllable switch to direct the sensed signal to the ECG processing circuitry includes ceasing providing of the injection current, and wherein actuation of the controllable switch to direct the sensed signal to the BI processing circuitry includes resuming providing of the injection current.

Example 15 is the system of example(s) 14, wherein actuation of the controllable switch to direct the sensed signal to the ECG processing circuitry further includes acquiring an additional sensed signal via the first pair of electrodes and determining additional ECG measurements from the additional sensed signal.

Example 16 is a method, comprising: providing an injection current at a first pair of electrodes; acquiring a sensed signal at a second pair of electrodes, wherein the first pair of electrodes and the second pair of electrodes are arranged in a linear array; and determining electrocardiogram (ECG) measurements and bioimpedance (BI) measurements from the sensed signal.

Example 17 is the method of example(s) 16, wherein the second pair of electrodes are positioned within a space defined between each electrode of the first pair of electrodes.

Example 18 is the method of example(s) 16 or 17, wherein the first pair of electrodes and the second pair of electrodes are incorporated into a wearable device, and wherein the first pair of electrodes and the second pair of electrodes are each electrically couplable to skin of a user wearing the wearable device.

Example 19 is the method of example(s) 18, wherein the wearable device is a patch having a patch substrate, wherein the first pair of electrodes and the second pair of electrodes are embedded within the patch substrate, and wherein the patch substrate includes an adhesive layer to secure the patch against the skin of the user.

Example 20 is the method of example(s) 19, wherein the patch substrate further comprises conductive gel disposed on respective exposed surfaces of each of the electrodes of the first pair of electrodes and the second pair of electrodes.

Example 21 is the method of example(s) 18-20, wherein the wearable device is waterproof or water-resistant, and wherein the wearable device is configured to be worn by the user in a wet environment.

Example 22 is the method of example(s) 16-21, wherein determining the ECG measurements and the BI measurements from the sensed signal includes: determining an ECG signal from the sensed signal; and determining a BI signal from the sensed signal.

Example 23 is the method of example(s) 22, wherein determining the ECG signal from the sensed signal includes filtering the sensed signal to extract the ECG signal from the sensed signal, and wherein determining the BI signal from the sensed signal includes filtering the sensed signal to extract the BI signal from the sensed signal.

Example 24 is the method of example(s) 22 or 23, wherein determining the ECG measurements and the BI measurements from the sensed signal further includes: down-converting the BI signal; and processing the down-converted BI signal to extract the BI measurements.

Example 25 is the method of example(s) 24, wherein providing the injection current via the first pair of electrodes includes injecting a current at or greater than an injection frequency, and wherein down-converting the BI signal includes down-converting the BI signal to a frequency at or below the injection frequency.

Example 26 is the method of example(s) 25, wherein down-converting the BI signal includes down-converting the BI signal to a frequency at or below 1 kHz.

Example 27 is the method of example(s) 22, wherein determining the ECG signal from the sensed signal includes actuating a controllable switch to direct the sensed signal to ECG processing circuitry, and wherein determining the BI signal from the sensed signal includes actuating the controllable switch to direct the sensed signal to BI processing circuitry.

Example 28 is the method of example(s) 27, further comprising providing a clock signal to the controllable switch to actuate the controllable switch.

Example 29 is the method of example(s) 27 or 28, further comprising: ceasing providing of the injection current in response to actuation of the controllable switch to direct the sensed signal to the ECG processing circuitry; and resuming providing of the injection current in response to actuation of the controllable switch to direct the sensed signal to the BI processing circuitry.

Example 30 is the method of example(s) 29, further comprising: acquiring an additional sensed signal via the first pair of electrodes in response to actuation of the controllable switch to direct the sensed signal to the ECG processing circuitry; and determining additional ECG measurements from the additional sensed signal.

Example 31 is a computer-program product tangibly embodied in a non-transitory machine-readable storage medium, including instructions configured to cause a data processing apparatus to perform the method of example(s) 16-30.

Example 32 is a system for monitoring glucose levels of a patient, the system comprising: at least two electrodes configured to output electrical data; a display; a memory; a control system coupled to the memory comprising one or more processors, the control system configured to execute the machine executable code to cause the control system to: determine a first set of electrocardiogram features with machine executable code configured to cause the control system to: receive a set of electrical data output from the at least two electrodes; process the set of electrical data to output a set of electrocardiogram features; and store the electrocardiogram features in the memory; determine a first bioimpedance spectroscopy-based measurement with machine executable code configured to cause the control system to: send instructions to the electronic control system to apply a sinusoidal voltage to the at least two electrodes; determine a set of bioimpedance measurements based on electrical data output from the at least two electrodes; and store the set of bioimpedance measurements in the memory.

Example 33 is the system of example(s) 32, further comprising machine executable code configured to cause the control system to: process the set of electrocardiogram features to output an ECG-based blood glucose level and store the ECG-based blood glucose level in the memory; process the set of bioimpedance measurements to output a bioimpedance-based glucose level and store the bioimpedance-based glucose level in the memory; process the bioimpedance-based glucose level and the ECG-based blood glucose level to output an adapted glucose level and store the adapted glucose level in memory; and display the adapted glucose level on a display.

Example 34 is the system of example(s) 32 or 33, wherein the set of electrocardiogram features comprises amplitude differences between electrocardiogram points.

Example 35 is the system of example(s) 32-34, wherein the set of electrocardiogram features comprises a QS amplitude, a QR amplitude, a TR amplitude, and an ST amplitude.

Example 36 is the system of example(s) 35, wherein the set of electrocardiogram features further comprises a Q-T interval and a Q-S interval.

Example 37 is the system of example(s) 36, wherein process the set of electrocardiogram features further comprises process the electrocardiogram features according to the equation C1*(the QS amplitude/the QR amplitude+the TR amplitude/the ST amplitude)+C2*(the Q-T interval/the Q-S interval).

Example 38 is the system of example(s) 37, wherein C1 and C2 are determined by experimentation using a data set output from an invasive glucose meter reading.

Example 39 is the system of example(s) 32-38, further comprising an electronic control system connected to the at least two electrodes and configured to control a voltage applied to the at least two electrodes.

Example 40 is the system of example(s) 32-39, wherein apply a sinusoidal voltage comprises applying a set of sinusoidal frequencies in the range of 1 kHz-200 MHz.

Example 41 is the system of example(s) 33-40, wherein process the set of bioimpedance measurements to output the bioimpedance-based glucose level further comprises the calibration with temperature values, amplitudes of QRS complex values, and heart rate values using a linear equation.

Example 42 is the system of example(s) 33-41, wherein process the bioimpedance-based glucose level and ECG-based glucose level to output an adapted glucose level comprises combining the bioimpedance-based glucose level and the ECG-based glucose level with a linear formula.

Example 43 is the system of example(s) 42, wherein the linear formula comprises summing the bioimpedance-based glucose level multiplied by a first coefficient and the ECG-based glucose level multiplied by a second coefficient.

Example 44 is a system for monitoring glucose levels of a patient, the system comprising: a set of two electrodes; a display; a memory; a control system coupled to the memory comprising one or more processors, the control system configured to execute the machine executable code to cause the control system to: determine a first set of electrocardiogram features with machine executable code configured to cause the control system to: receive a set of electrical data output from the at least two electrodes; process the set of electrical data to output a set of electrocardiogram features; and store the electrocardiogram features in the memory; determine a first bioimpedance spectroscopy-based measurement with machine executable code configured to cause the control system to: send instructions to the electronic control system to apply a sinusoidal voltage to the at least two electrodes; determine a set of bioimpedance measurements based on electrical data output from the at least two electrodes; and store the set of bioimpedance measurements in the memory.

Example 45 is the system of example(s) 44, further comprising machine executable code configured to cause the control system to process the set of bioimpedance measurements to output a fluid volume estimation, or a body cell mass estimation.

Example 46 is the system of example(s) 44 or 45, wherein the set of at least two electrodes, the memory, and the control system are contained in a wearable device configured to be attached to a patient.

Example 47 is the system of example(s) 46, wherein the at least two electrodes comprise only two electrodes.

Example 48 is the system of example(s) 47, wherein the wearable device is configured to be a wearable patch.

What is claimed is:

1. A system for monitoring glucose levels of a patient, the system comprising:
    at least two electrodes configured to output electrical data;
    a display;
    a memory;
    a control system coupled to the memory comprising one or more processors, the control system configured to execute machine executable code to cause the control system to:
    determine a first set of electrocardiogram features, wherein determining the first set of electrocardiogram features includes causing the control system to:
    receive a set of electrical data output from the at least two electrodes;
    process the set of electrical data to output a set of electrocardiogram features, wherein the set of electrocardiogram features comprises a QS amplitude, a QR amplitude, a TR amplitude, an ST amplitude, a Q-T interval, and a Q-S interval; and
    store the electrocardiogram features in the memory;
    determine a first bioimpedance spectroscopy (BIS) measurement, wherein determining the first BIS measurement includes causing the control system to:
    send instructions to the electronic control system to apply a sinusoidal voltage to the at least two electrodes;
    determine a set of BIS measurements based on electrical data output from the at least two electrodes; and
    store the set of BIS measurements in the memory; and
    determine a blood glucose level using the first set of electrocardiogram features and the first BIS measurement.

2. The system of claim 1, wherein determining the blood glucose level further comprises:
    processing the set of electrocardiogram features to output an ECG-based blood glucose level and store the ECG-based blood glucose level in the memory;
    processing the set of BIS measurements to output a bioimpedance based BIS-based blood glucose level and store the BIS-based blood glucose level in the memory;
    processing the BIS-based blood glucose level and the ECG-based blood glucose level to output an adapted blood glucose level and store the adapted blood glucose level in memory; and
    displaying the adapted blood glucose level on the display.

3. The system of claim 1, wherein the set of electrocardiogram features comprises a set of amplitude differences, wherein each of the set of amplitude differences represents a difference in amplitude between a first electrocardiogram point and a second electrocardiogram point.

4. The system of claim 1, wherein processing the set of electrocardiogram features further comprises processing the electrocardiogram features according to the equation C1 * (the QS amplitude/the QR amplitude+the TR amplitude/the ST amplitude)+C2 * (the Q-T interval/the Q-S interval), wherein C1 and C2 are constants.

5. The system of claim 4, wherein C1 and C2 are experimentally determined constants based on invasive blood glucose readings.

6. The system of claim 1, further comprising an electronic control system connected to the at least two electrodes and configured to control a voltage applied to the at least two electrodes.

7. The system of claim 1, wherein applying the sinusoidal voltage comprises applying a set of sinusoidal frequencies in the range of 1 kHz 200 MHz.

8. The system of claim 2, wherein processing the set of BIS measurements to output the BIS-based blood glucose level further comprises calibration with temperature values, amplitudes of QRS complex values, and heart rate values using a linear equation.

9. The system of claim 2, wherein processing the BIS-based blood glucose level and ECG-based blood glucose level to output the adapted blood glucose level comprises combining the BIS-based blood glucose level and the ECG-based blood glucose level with a linear formula.

10. The system of claim 9, wherein the linear formula comprises summing the BIS-based blood glucose level multiplied by a first coefficient and the ECG-based blood glucose level multiplied by a second coefficient.

11. A system for monitoring glucose levels of a patient, the system comprising:
   a set of two electrodes;
   a display;
   a memory;
   a control system coupled to the memory comprising one or more processors, the control system configured to execute machine executable code to cause the control system to:
   determine a first set of electrocardiogram features with machine executable code configured to cause the control system to:
   receive a set of electrical data output from the at least two electrodes;
   process the set of electrical data to output a set of electrocardiogram features, wherein the set of electrocardiogram features comprises a QS amplitude, a QR amplitude, a TR amplitude, an ST amplitude, a Q-T interval, and a Q-S interval; and
   store the electrocardiogram features in the memory;
   determine a first bioimpedance spectroscopy (BIS) measurement with machine executable code configured to cause the control system to:
   send instructions to the electronic control system to apply a sinusoidal voltage to the at least two electrodes;
   determine a set of BIS measurements based on electrical data output from the at least two electrodes; and
   store the set of BIS measurements in the memory; and
   determine a blood glucose level using the first set of electrocardiogram features and the first BIS measurement.

12. The system of claim 11, further comprising machine executable code configured to cause the control system to process the set of BIS measurements to output a fluid volume estimation, or a body cell mass estimation.

13. The system of claim 11, wherein the set of at least two electrodes, the memory, and the control system are contained in a wearable device configured to be attached to a patient.

14. The system of claim 13, wherein the at least two electrodes comprise only two electrodes.

15. The system of claim 14, wherein the wearable device is configured to be a wearable patch.

16. A system for monitoring glucose levels of a patient, the system comprising:
   at least two electrodes configured to output electrical data;
   a memory;
   a control system coupled to the memory comprising one or more processors, the control system configured to perform operations including:
   determining a first set of electrocardiogram (ECG) features, wherein determining the first set of ECG features includes:
   receiving a set of electrical data output from the at least two electrodes;
   processing the set of electrical data to output a set of ECG features comprising a QS amplitude, a QR amplitude, a TR amplitude, an ST amplitude, a Q-T interval, and a Q-S interval; and
   storing the ECG features in the memory;
   determining a first bioimpedance spectroscopy (BIS) measurement, wherein determining the first BIS measurement includes:
   sending instructions to the electronic control system to apply a sinusoidal voltage to the at least two electrodes;
   determining a set of BIS measurements based on electrical data output from the at least two electrodes; and
   storing the set of BIS measurements in the memory;
   determining an ECG-based blood glucose level using the set of ECG features;
   determining a BIS-based blood glucose level using the set of BIS measurements; and
   determining an adapted blood glucose level based on the ECG-based blood glucose level and the BIS-based blood glucose level.

17. The system of claim 16, wherein determining the ECG-based blood glucose level using the set of ECG features includes applying the equation t,? wherein $BG_{ECG}$ is the ECG-based blood glucose level, C1 is a first constant, and C2 is a second constant.

18. The system of claim 17, wherein C1 and C2 are determined by experimentation using a data set containing invasive blood glucose readings.

* * * * *